US012718951B2

(12) United States Patent
Yu et al.

(10) Patent No.: US 12,718,951 B2
(45) Date of Patent: Aug. 25, 2026

(54) AMBULATORY GLUCOSE PROFILE (AGP) INTELLIGENT INTERPRETATION AND INSULIN ADJUSTMENT METHOD BASED ON EXPERT SYSTEM

(71) Applicants: Northeastern University, Shenyang (CN); Shanghai Sixth People's Hospital, Shanghai (CN)

(72) Inventors: Xia Yu, Shenyang (CN); Hongru Li, Shenyang (CN); Xiaoyu Sun, Shenyang (CN); Jian Zhou, Shanghai (CN); Jingyi Lu, Shanghai (CN); Xiaojing Ma, Shanghai (CN)

(73) Assignees: Northeastern University, Shenyang (CN); Shanghai Sixth People's Hospital, Shanghai (CN)

( * ) Notice: Subject to any disclaimer, the term of this patent is extended or adjusted under 35 U.S.C. 154(b) by 0 days.

(21) Appl. No.: 19/312,360

(22) Filed: Aug. 28, 2025

(65) Prior Publication Data

US 2026/0088171 A1 Mar. 26, 2026

(30) Foreign Application Priority Data

Sep. 25, 2024 (CN) ......................... 202411338290.0

(51) Int. Cl.
*G16H 50/20* (2018.01)
*A61M 5/172* (2006.01)

(Continued)

(52) U.S. Cl.
CPC .......... *G16H 50/20* (2018.01); *A61M 5/1723* (2013.01); *G01N 33/49* (2013.01); *G16H 20/17* (2018.01);

(Continued)

(58) Field of Classification Search
None
See application file for complete search history.

(56) References Cited

U.S. PATENT DOCUMENTS

| | | | | |
|---|---|---|---|---|
| 2021/0290113 | A1* | 9/2021 | Liu | A61B 5/14532 |
| 2022/0386965 | A1* | 12/2022 | Kovatchev | G16H 50/20 |
| 2025/0072793 | A1* | 3/2025 | Kovatchev | G16H 50/70 |

FOREIGN PATENT DOCUMENTS

| | | |
|---|---|---|
| CN | 117038062 A | 11/2023 |
| CN | 117099165 A | 11/2023 |

(Continued)

OTHER PUBLICATIONS

Rose Lin et al., The ambulatory glucose profile and its interpretation, 217 Medical Journal of Australia, 295-298 (2022), https://www.mja.com.au/system/files/issues/217_06/mja251666.pdf (last visited Mar. 19, 2026) (Year: 2022).*

(Continued)

*Primary Examiner* — Jonathon A. Szumny
*Assistant Examiner* — Nicholas Akogyeram, II
(74) *Attorney, Agent, or Firm* — Bayramoglu Law Offices LLC

(57) ABSTRACT

An ambulatory glucose profile (AGP) intelligent interpretation and insulin adjustment method based on an expert system includes: establishing a knowledge base in an inference mechanism; constructing an interpretation and decision support expert system with a simplified expert system architecture based on the knowledge base; constructing a patient problem analysis tree in three dimensions of hypoglycemia, blood glucose fluctuation, and hyperglycemia of patients; expanding each rule with expert AGP interpretation and empirical data; constructing a basal insulin dosage adjustment rule and a mealtime insulin dosage adjustment rule based on an interval type-2 fuzzy expert system; and adjusting a node of the patient problem analysis tree based on the (Continued)

interpretation and decision support expert system and a group of the patient, and providing a decision suggestion in combination with the basal insulin dosage adjustment rule and the mealtime insulin dosage adjustment rule.

18 Claims, 11 Drawing Sheets

(51) Int. Cl.

| | |
|---|---|
| ***G01N 33/49*** | (2006.01) |
| ***G16H 20/17*** | (2018.01) |
| ***G16H 70/40*** | (2018.01) |

(52) U.S. Cl.

CPC ....... *G16H 70/40* (2018.01); *A61M 2230/201* (2013.01)

(56) References Cited

FOREIGN PATENT DOCUMENTS

| | | | | | |
|---|---|---|---|---|---|
| CN | 118538356 | A | | 8/2024 | |
| KR | 20230114553 | A | | 8/2023 | |
| WO | WO-2023212076 | A1 | * | 11/2023 | ............. G16H 20/10 |

OTHER PUBLICATIONS

Chinese Diabetes Society, Chinese clinical guideline for continuous glucose monitoring (2017), Chinese Journal of Diabetes Mellitus, 2017, pp. 667-675, vol. 9, No. 11.

Chinese Society of Endocrinology, et al., Expert consensus on the clinical application of ambulatory glucose profile report (2023 edition), Chinese Journal of Diabetes Mellitus, 2024, pp. 190-201, vol. 16, No. 2.

Obstetrics Subgroup, Chinese Society of Obstetrics and Gynecology, Chinese Medical Association, et al., Guideline of diagnosis and treatment of hyperglycemia in pregnancy (2022) [Part one], Chinese Journal of Obstetrics and Gynecology, 2022, pp. 3-12, vol. 57, No. 1.

Obstetrics Subgroup, Chinese Society of Obstetrics and Gynecology, Chinese Medical Association, et al., Guideline of diagnosis and treatment of hyperglycemia in pregnancy (2022) [Part two], Chinese Journal of Obstetrics and Gynecology, 2022, pp. 81-90, vol. 57, No. 2.

Li Guang-Wei, Management and Strategy of Hyperglycemia in Hospitalized Patients, Drug Evaluation, 2017, pp. 5-8, vol. 14, No. 13.

Eric Johnson, et al., Diabetes update: Your guide to the latest ADA standards, Journal of Family Practice, 2016, pp. 310-318, vol. 65, No. 5.

* cited by examiner $d_1$
$d_2$
1.0
0.5
0.0
μ(d)
0.00
0.25
0.50
0.75
1.00
d

AMBULATORY GLUCOSE PROFILE (AGP) INTELLIGENT INTERPRETATION AND INSULIN ADJUSTMENT METHOD BASED ON EXPERT SYSTEM

CROSS REFERENCE TO THE RELATED APPLICATIONS

This application is based upon and claims priority to Chinese Patent Application No. 202411338290.0, filed on Sep. 25, 2024, the entire contents of which are incorporated herein by reference.

TECHNICAL FIELD

The present disclosure relates to the technical field of blood glucose control, and in particular to an ambulatory glucose profile (AGP) intelligent interpretation and insulin adjustment method based on an expert system.

BACKGROUND

As a standardized glucose detection report universally recommended by worldwide guidelines, the AGP contains comprehensive blood glucose information of diabetic patients. Accurate interpretation of AGP can guide clinical treatment of the patients. However, due to omission of some key information in the glucose profile and index summary, analysts may ignore true patterns of the patients, and need to carefully view daily profiles for event annotation and analysis. This leads to a contradiction between accuracy and time cost, and requires a large amount of expert knowledge.

To analyze AGP, multiple expert clinical guidelines have been formulated worldwide. Meanwhile, digital therapeutics, such as use of blood glucose fluctuation parameters for identifying type 1 diabetes and type 2 diabetes, and an automatic meal detection and carbohydrate estimation method based on an artificial intelligence (AI) model, are constantly being developed and applied for assisting clinical decision-making, revealing the application prospect of the AI in the AGP.

When the clinical "five-step" method proposed in the latest guideline in China is used to interpret the AGP, by evaluating an overall blood glucose level, a hypoglycemia risk, glycemic variability (GV), and a hyperglycemia risk, medications such as insulin of the patient are adjusted, and suggestions for improving the lifestyle are proposed. However, the existing profile interpretation and decision support have the following problems:

Although the glucose profile is more intuitive for doctors and patients to know blood glucose conditions over multiple days, some blood glucose information of the patients is still omitted, and careful analysis on the daily profiles is still essential. To complete this process, accurate expert knowledge and a great deal of time and energy are required. During this process, the blood glucose levels (BGLs) of the patients are determined through a strict threshold and are absolute, but decisions of the experts in many cases are flexible.

There are relatively few studies on automated systems that help users interpret the AGP and provide optimal management suggestions. Due to significantly different lifestyles, physiological statuses, insulin sensitivities and the like of the patients, the BGLs are affected by various factors, including diets, exercises, and medications. Without fully considering individual differences of the patients, the conventional general treatment methods cannot provide personalized treatment decisions.

In the process of reviewing data to make the personalized treatment decisions, the doctors and patients not only focus on whether the insulin dosage is adjusted, but also on how much the insulin dosage is adjusted. Improper insulin administration can lead to transient and severe hypoglycemia and hyperglycemia, or even diabetic ketoacidosis. In existing expert guidelines in China, there are no specific rules to adjust the insulin dosage based on multi-day blood glucose monitoring data of the patients.

SUMMARY

Technical Problem to be Solved

In view of the above defects and shortcomings of the prior art, the present disclosure provides an AGP intelligent interpretation and insulin adjustment method based on an expert system, to solve the technical problem that in existing expert guidelines, there are no specific rules to adjust an insulin dosage based on multi-day blood glucose monitoring data of the patients.

Technical Solutions

To achieve the above objective, main technical solutions adopted by the present disclosure are as follows:

According to a first aspect, the present disclosure provides an AGP intelligent interpretation and insulin adjustment method based on an expert system, including:

based on an AGP and an inference mechanism of a top-down forward inference strategy, establishing a knowledge base in the inference mechanism;

constructing an interpretation and decision support expert system with a simplified expert system architecture based on the knowledge base;

based on a fault tree analysis (FTA) method and an expert guideline, constructing a patient problem analysis tree in three dimensions of hypoglycemia, blood glucose fluctuation, and hyperglycemia of patients, each branch of the patient problem analysis tree being corresponding to one or more rules;

expanding each rule with expert AGP interpretation and empirical data;

grouping the patients with a K-means clustering algorithm;

constructing a basal insulin dosage adjustment rule and a mealtime insulin dosage adjustment rule based on an interval type-2 fuzzy expert system; and adjusting a node of the patient problem analysis tree based on the interpretation and decision support expert system and a group of the patient, and providing a decision suggestion in combination with the basal insulin dosage adjustment rule and the mealtime insulin dosage adjustment rule.

Optionally, the simplified expert system architecture includes the knowledge base, a database, a human-machine interface (HMI), and the inference mechanism;

the knowledge base is used to store a patient interpretation rule and a decision rule based on the AGP;

the database is used to store personal information and blood glucose data of the patient;

the HMI is used to transmit information of the patient to a system and display an AGP report; and the inference mechanism is used to perform inference with a rule and an index calculated from data in the knowledge base to obtain a content of the AGP report of the patient and output the content.

Optionally, the establishing a knowledge base in the inference mechanism includes:

checking data sufficiency, viewing an overall blood glucose level, and evaluating a hypoglycemia risk, GV, and a hyperglycemia risk, thereby obtaining the knowledge base in the inference mechanism.

Optionally, the grouping the patients with a K-means clustering algorithm includes:

for a continuous glucose monitor (CGM) matrix $X \in R^{M \times N}$ of the patients, extracting glucose symbolic pattern (GSP) features based on domain knowledge;

with the GSP features as an input, obtaining possible clusters of the patients by using a K-means clustering algorithm, taking K=4 as a final class number, and inputting the GSP features and a K value to the K-means clustering algorithm; and until the K-means clustering algorithm converges, outputting clusters of the patients, and dividing the patients into four subtype groups T1, T2, T3 and T4 according to clinical significance.

Optionally, the constructing a basal insulin dosage adjustment rule based on an interval type-2 fuzzy expert system includes:

in combination with a basal insulin adjustment rule, taking a fasting blood-glucose (FBG) median, a proportion of days with nocturnal blood glucose in a hypoglycemic range, a proportion of days with nocturnal blood glucose elevated, and a proportion of days with nocturnal blood glucose in a hyperglycemic range as system input indexes;

taking 7.2 mmol/L as a cutoff point for elevated FBG of patients with type 1 diabetes or type 2 diabetes, calculating daily FBG according to mean blood glucose (MBG) in a range [6, min($t_z$, 8)], and assuming a basal insulin adjusted dosage as a system output, where, $t_z$ is breakfast starting time predicted through a mealtime detection algorithm, and the mealtime detection algorithm is implemented by generating and preprocessing a dataset, training a neural network to obtain an optimal model, and applying the optimal model to a test set to filter and output a most possible mealtime point to serve as the breakfast starting time;

establishing a membership function for each index with an interval type-2 fuzzy set dominated by a triangle and followed by a trapezoid; and formulating a rule for dosage adjustment on basal insulin of the patient with a fuzzy logic based on the membership function, where the rule is preferentially formulated according to probabilities of hyperglycemia and hypoglycemia at nighttime, and then the rule is formulated for the dosage adjustment according to the FBG median.

Optionally, the constructing a mealtime insulin dosage adjustment rule based on an interval type-2 fuzzy expert system includes:

in combination with a mealtime insulin adjustment rule, taking a median for differences between 2-h postprandial blood glucose and preprandial blood glucose over multiple days, a proportion of days with next preprandial or pre-sleep blood glucose in a hypoglycemic range, and a proportion of days with next preprandial or pre-sleep blood glucose in an FBG elevated range as system input indexes;

calculating the difference between the 2-h postprandial blood glucose and the preprandial blood glucose according to a difference between a blood glucose value 2 h after mealtime and a blood glucose value 30 min before the mealtime, and assuming a mealtime insulin adjusted dosage as a system output;

establishing a membership function for each index with an interval type-2 fuzzy set dominated by a triangle and followed by a trapezoid; and formulating a rule for dosage adjustment on mealtime insulin of a diabetic patient with a fuzzy logic based on the membership function, where the rule is preferentially formulated according to probabilities of hyperglycemia and hypoglycemia before a next meal or a next sleep, and then the rule is formulated for the dosage adjustment according to the median for the differences between the 2-h postprandial blood glucose and the preprandial blood glucose.

Optionally, the method further includes:

if an insulin dosage adjustment suggestion is adopted by the patient in a previous period to adjust basal insulin $\alpha$ IU, and mealtime insulin $\beta$ IU, calculating suggested basal insulin $\lambda$ IU and suggested mealtime insulin $\gamma$ IU with an interval type-2 fuzzy expert system of the previous period in a present period; and updating parameters of a membership function based on $\lambda$ and $\gamma$, and determining an insulin dosage adjustment suggestion in the present period based on an updated membership function.

According to a second aspect, the present disclosure provides a computer-readable storage medium, where the computer-readable storage medium stores a computer program; and when the computer program is executed, the AGP intelligent interpretation and insulin adjustment method based on an expert system in the first aspect is implemented.

According to a third aspect, the present disclosure provides a storage device, including a storage medium and a processor, where the storage medium stores a computer program; and when the computer program is executed by the processor, the AGP intelligent interpretation and insulin adjustment method based on an expert system in the first aspect is implemented.

Beneficial Effects

The present disclosure has the following beneficial effects: The AGP intelligent interpretation and insulin adjustment method based on an expert system provided by the present disclosure quickly locates the problem of the patient in combination with expert knowledge in the medical field, and establishes an expert system that helps the doctor make a decision and help the patient understand a blood glucose condition more clearly. The system can provide a highly personalized intelligent decision suggestion for the patient with different blood glucose control conditions, and provides a safe, universal, and relatively accurate insulin adjustment decision suggestion for the patient without a specific initial insulin treatment scheme of the patient.

BRIEF DESCRIPTION OF THE DRAWINGS

FIG. 4B is continuous with FIG. 4A;

DETAILED DESCRIPTION OF THE EMBODIMENTS

Figure 1:
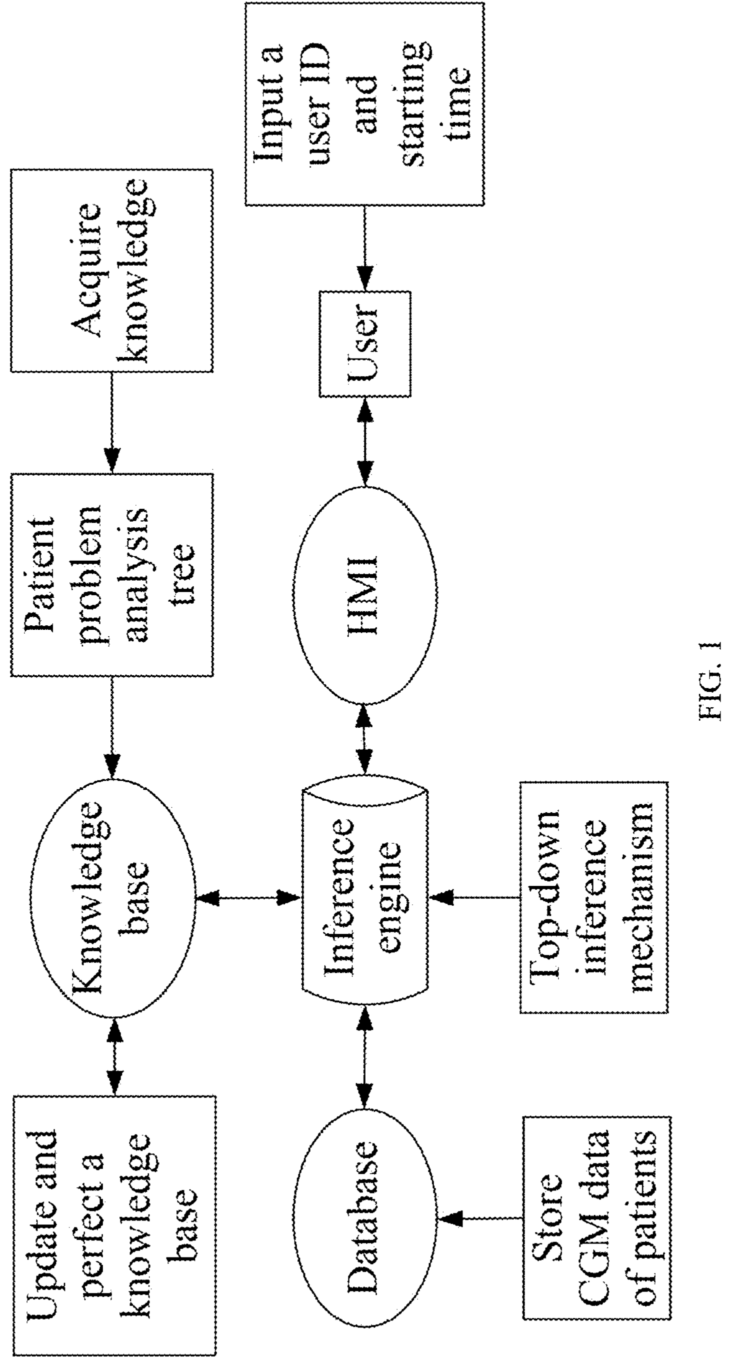
FIG. 1 is a schematic structural view of an interpretation and decision support expert system constructed according to an embodiment of the present disclosure.

To facilitate a better understanding of the present disclosure, the present disclosure is described in detail below with reference to the accompanying drawings and specific implementations.

An embodiment of the present disclosure provides an AGP intelligent interpretation and insulin adjustment method based on an expert system, including: construction of an interpretation and decision support expert system, construction of an intelligent patient problem analysis tree, and construction of "basal+mealtime" insulin dosage adjustment rules based on an interval type-2 fuzzy expert system.

Compared with the related art, based on historical blood glucose data of a diabetic patient, the present disclosure performs intelligent interpretation on a CGM profile of the patient and provides personalized aided decision support. First of all, the method can be convenient for the expert and the patient to know a blood glucose condition over multiple days more intuitively, without omitting blood glucose information of the patient. This process does not need relatively complex expert knowledge and a great deal of time and energy. In this process, the BGL of the patient is determined flexibly. Then, the method enhances relevance of the decision, and further provides a customized health management scheme for each patient, thereby optimizing the treatment effect, preventing the redundant decision suggestion, and improving the life quality of the patient. At last, the method can better adapt to different patients or blood glucose control conditions of the same patient in different blood glucose statuses, while ensuring the safety. The method can be widely applied to the blood glucose management field of the diabetic patient.

In order to facilitate a better understanding of the above technical solutions, the exemplary embodiments of the present disclosure are described in more detail below with reference to the accompanying drawings. Although the accompanying drawings show exemplary embodiments of the present disclosure, it should be understood that the present disclosure may be implemented in various forms and should not be limited to the embodiments set forth herein. The embodiments are provided for a more thorough understanding of the present disclosure, so as to make the scope of the present disclosure be fully conveyed to those skilled in the art.

According to a first aspect, an embodiment provides an AGP intelligent interpretation and insulin adjustment method based on an expert system, including:

S1, based on an AGP and an inference mechanism of a top-down forward inference strategy, a knowledge base in the inference mechanism is established.

S2, an interpretation and decision support expert system is constructed with a simplified expert system architecture based on the knowledge base.

This system can guide an analyst to interpret the profile according to steps. On the basis of clinical core indexes and other carefully selected indexes, while introducing statistical indexes based on a scenario period, and determining daily hyperglycemic and hypoglycemic events, the system solves the problem that the AGP depends on data integrity and AGP fluctuations arising from different mealtime throughout a day are explained hardly.

S3, based on an FTA method and an expert guideline, a patient problem analysis tree in three dimensions of hypoglycemia, blood glucose fluctuation, and hyperglycemia of patients, is constructed, each branch of the patient problem analysis tree being corresponding to one or more rules.

Based on the above expert system, and in combination with a latest expert consensus on AGP interpretation and an adjustment rule in a diabetes treatment scheme, the patient problem analysis tree capable of adjusting a node intelligently is constructed, thereby outputting a personalized decision suggestion. In view of individual differences of the patients, and pertinence of the provided decision, for the patients with different blood glucose control conditions, the method can intelligently adjusts the node of the patient problem analysis tree, so as to provide the highly personalized intelligent decision suggestion. The method enhances relevance of the decision, and further provides a customized health management scheme for each patient, thereby optimizing the treatment effect, preventing the redundant decision suggestion, and improving the life quality of the patient.

S4, each rule is expanded with expert AGP interpretation and empirical data. The empirical data is empirical data adjusted according to causes of diseases in the past.

S5, the patients are grouped with a K-means clustering algorithm.

S6, a basal insulin dosage adjustment rule and a mealtime insulin dosage adjustment rule are constructed based on an interval type-2 fuzzy expert system.

S7, a node of the patient problem analysis tree is adjusted based on the interpretation and decision support expert system and a group of the patient, and a decision suggestion is provided in combination with the basal insulin dosage adjustment rule and the mealtime insulin dosage adjustment rule.

On the basis of the proposed insulin dosage adjustment rules, fuzzy inference is introduced. The uncertain conceptual rule is introduced to serve as a fuzzy rule, which provides a safe, universal, and relatively accurate insulin adjustment decision suggestion for the patient, without a specific initial insulin treatment scheme of the patient. Upon this, a simple incremental learning method is used. With repeated periodic adjustment, parameters of the fuzzy inference system can be adjusted according to a blood glucose improved condition of the patient.

Optionally, the simplified expert system architecture includes the knowledge base, a database, an HMI, and the inference mechanism.

The knowledge base is used to store a patient interpretation rule and a decision rule based on the AGP.

The database is used to store personal information and blood glucose data of the patient.

The HMI is used to transmit information of the patient to a system and display an AGP report.

The inference mechanism is used to perform inference with a rule and an index calculated from data in the knowledge base to obtain a content of the AGP report of the patient and output the content.

Optionally, the step that a knowledge base in the inference mechanism is established includes:

Data sufficiency is checked, an overall blood glucose level is viewed, and a hypoglycemia risk, GV, and a hyperglycemia risk are evaluated, thereby obtaining the knowledge base in the inference mechanism.

Optionally, the step that the patients are grouped with a K-means clustering algorithm includes:

For a CGM matrix $X \in R^{M \times N}$ of the patients, GSP features are extracted based on domain knowledge.

With the GSP features as an input, possible clusters of the patients are obtained by using a K-means clustering algorithm, K=4 is taken as a final class number, and the GSP features and a K value are input to the K-means clustering algorithm.

Until the K-means clustering algorithm converges, clusters of the patients are output, and the patients are divided into four subtype groups T1, T2, T3 and T4 according to clinical significance.

Optionally, the step that a basal insulin dosage adjustment rule is constructed based on an interval type-2 fuzzy expert system includes:

In combination with two basal insulin adjustment rules (the basal insulin adjustment rules are respectively shown in Table 17 and Table 18), an FBG median, a proportion of days with nocturnal blood glucose in a hypoglycemic range, a proportion of days with nocturnal blood glucose elevated, and a proportion of days with nocturnal blood glucose in a hyperglycemic range are taken as system input indexes.

7.2 mmol/L is taken as a cutoff point for elevated FBG of patients with type 1 diabetes or type 2 diabetes, daily FBG is calculated according to MBG in a range [6, min($t_z$, 8)], and a basal insulin adjusted dosage is assumed as a system output, where, $t_z$ is breakfast starting time predicted through a mealtime detection algorithm, and the mealtime detection algorithm is implemented by generating and preprocessing a dataset, training a neural network to obtain an optimal model, and applying the optimal model to a test set to filter and output a most possible mealtime point to serve as the breakfast starting time.

A membership function for each index is established with an interval type-2 fuzzy set dominated by a triangle and followed by a trapezoid.

A rule is formulated for dosage adjustment on basal insulin of the patient with a fuzzy logic based on the membership function, where the rule is preferentially formulated according to probabilities of hyperglycemia and hypoglycemia at nighttime, and then the rule is formulated for the dosage adjustment according to the FBG median.

Optionally, the step that a mealtime insulin dosage adjustment rule is constructed based on an interval type-2 fuzzy expert system includes:

In combination with two mealtime insulin adjustment rules (the mealtime insulin adjustment rules are respectively shown in Table 20 and Table 21), a median for differences between 2-h postprandial blood glucose and preprandial blood glucose over multiple days, a proportion of days with next preprandial or pre-sleep blood glucose in a hypoglycemic range, and a proportion of days with next preprandial or pre-sleep blood glucose in an FBG elevated range are taken as system input indexes.

The difference between the 2-h postprandial blood glucose and the preprandial blood glucose is calculated according to a difference between a blood glucose value 2 h after mealtime and a blood glucose value 30 min before the mealtime, and a mealtime insulin adjusted dosage is assumed as a system output.

A membership function for each index is established with an interval type-2 fuzzy set dominated by a triangle and followed by a trapezoid.

A rule is formulated for dosage adjustment on mealtime insulin of a diabetic patient with a fuzzy logic based on the membership function, where the rule is preferentially formulated according to probabilities of hyperglycemia and hypoglycemia before a next meal or a next sleep, and then the rule is formulated for the dosage adjustment according to the median for the differences between the 2-h postprandial blood glucose and the preprandial blood glucose.

Optionally, the method further includes:

if an insulin dosage adjustment suggestion is adopted by the patient in a previous period to adjust basal insulin $\alpha$ IU, and mealtime insulin $\beta$ IU, suggested basal insulin $\lambda$ IU and suggested mealtime insulin $\gamma$ IU are calculated with an interval type-2 fuzzy expert system of the previous period in a present period.

Parameters of a membership function are updated based on $\lambda$ and $\gamma$, and an insulin dosage adjustment suggestion in the present period is determined based on an updated membership function.

The AGP intelligent interpretation and insulin adjustment method based on an expert system provided by the present disclosure is further described below in combination with a specific embodiment:

1. Construction of an Interpretation and Decision Support Expert System

As shown in FIG. 1, the method integrates an existing expert consensus, and analyzes the AGP from a daily profile to supplement information omitted in the AGP, quickly locating a problem of the patient, and establishing an expert system that helps the doctor make a decision and helps the patient understand a blood glucose condition more clearly.

A simplified expert system architecture, including a knowledge base, a database, an HMI, and an inference mechanism, is used, as shown in FIG. 1. The knowledge base is used to store a patient interpretation rule and a decision rule according to the AGP. The database is used to store personal information and blood glucose data of the patient. The HMI is mainly used to transmit information of the patient to a system and display an AGP report. The inference mechanism is used to perform inference with a rule and an index calculated from data in the knowledge base to obtain a content of the AGP report of the patient and output the content.

Figure 2:
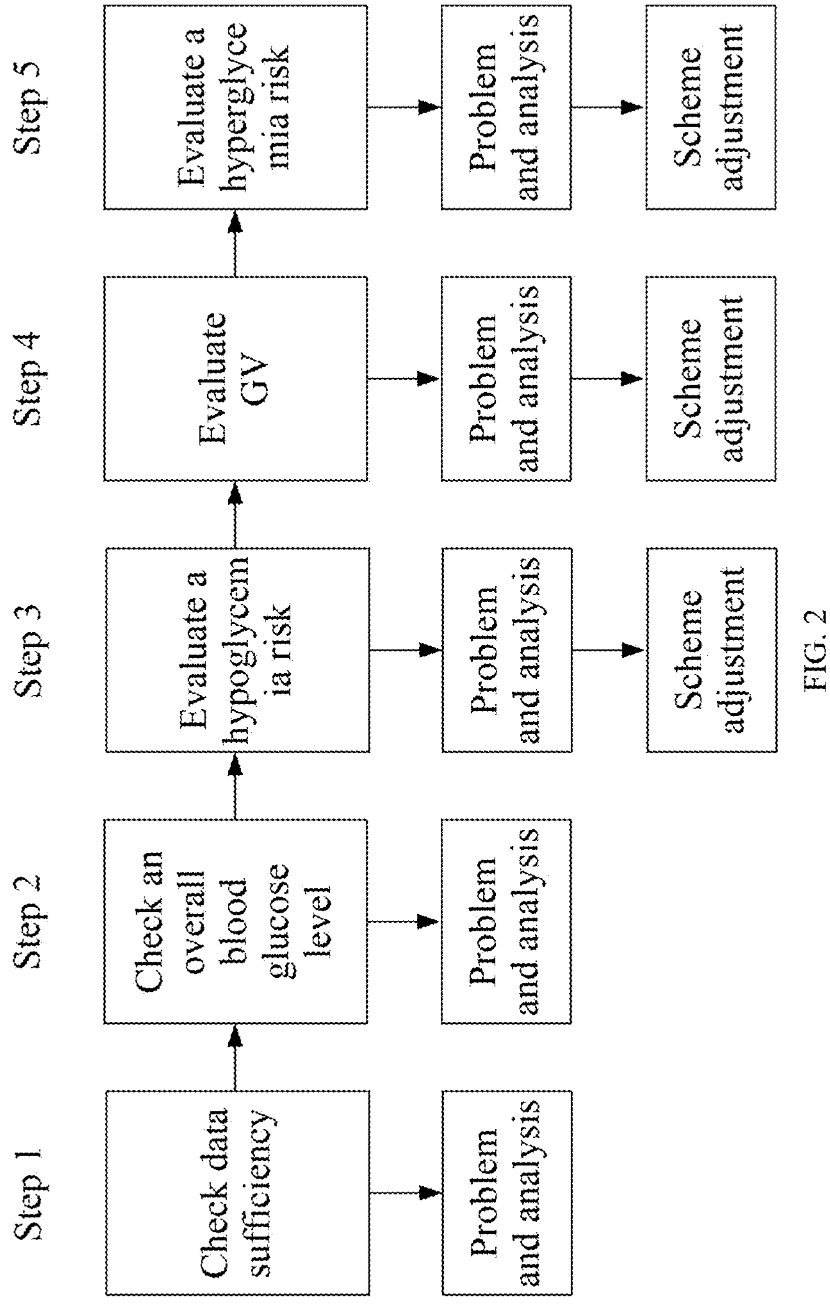
FIG. 2 is a schematic flowchart of a five-step method in an inference mechanism according to an embodiment of the present disclosure.

A top-down forward inference strategy from indexes of the AGP is used. That is, according to a known fact, a corresponding rule in the knowledge base is matched. A forward inference engine of the PyKnow is used, and the whole inference process is as shown in FIG. 2.

The specific analysis rule is as follows:

(1) Checking of Data Sufficiency and Analysis:

Assume that d is a number of CGM wearing days of the patient (days), and e is a proportion of valid CGM data (%). Table 1 illustrates evaluation on data sufficiency and an analysis rule.

TABLE 1

| Serial No. | Condition | Conclusion |
|---|---|---|
| 0101 | $d \geq 14$ and $e \geq 70$ | Data sufficiency |
| 0102 | $d < 14$ or $e < 70$ | Data insufficiency |

(2) Viewing of an Overall Blood Glucose Level and Analysis:

Assume that $t_1$ is time that a median line falls out of an interval range. The rule is shown in Table 2, where tir represents a threshold of time in range (TIR).

TABLE 2

| Serial No. | Condition | Conclusion |
|---|---|---|
| 0201 | MG < 8.5 and TIR ≥ tir and $t_1 = 0$ | Normal blood glucose |
| 0202 | MG ≥ 8.5 or TIR < tir or $t_1 > 0$ | Abnormal blood glucose |

(3) Evaluation on a Hypoglycemia Risk and Analysis:

With reference to expert concepts, a hypoglycemia risk evaluation rule is designed, as shown by 0301-0308 in Table 3. Patients with different types of diabetes each use personalized time below range (TBR) and a personalized threshold. Assume that a ventile is located at time $t_2$ in the hypoglycemic range.

TABLE 3

| Rule No. | Condition | Conclusion |
|---|---|---|
| 0301 | TBR < tbr and $TBR_2 < tbr_2$ and $t_2 = 0$ | Low hypoglycemia risk |
| 0302-0304 | TBR < tbr and TBR2 < tbr2 and $t_2 > 0$ or TBR < tbr and TBR2 ≥ tbr2 and $t_2 = 0$ Or TBR ≥ tbr and TBR2 < tbr2 and $t_2 = 0$ | Relatively low hypoglycemia risk |
| 0305-0307 | TBR < tbr and TBR2 ≥ tbr2 and $t_2 > 0$ or TBR ≥ tbr and TBR2 < tbr2 and $t_2 > 0$ or TBR ≥ tbr and TBR2 ≥ tbr2 and $t_2 = 0$ | Relatively hypoglycemia risk |
| 0308 | TBR ≥ tbr and TBR2 ≥ tbr2 and $t_2 > 0$ | Hypoglycemia risk |
| 0309-0313 | $n_{11} > 0$, $n_{12} > 0$, $n_{13} > 0$, $n_{14} > 0$, $n_{15} > 0$ | The hypoglycemia occurs at nighttime, before breakfast, lunch, dinner, and before sleep, with corresponding numbers of days being respectively $n_{11}$, $n_{12}$, $n_{13}$, $n_{14}$, and $n_{15}$. |
| 0314-0318 | $N_{21} > 0$, $n_{22} > 0$, $n_{23} > 0$, $n_{24} > 0$, $n_{25} > 0$ | The hypoglycemia occurs at nighttime, before breakfast, lunch, dinner, and before sleep, with corresponding numbers of days being respectively $n_{21}$, $n_{22}$, $n_{23}$, $n_{24}$, and $n_{25}$. |

In addition, in order to enhance information provided by the AGP, a hypoglycemic period throughout a day is determined according to scenario information. It is known that breakfast, lunch and dinner throughout the day are respectively taken at $t_x$, $t_w$ and $t_s$, and the preprandial period, the nighttime period and the bedtime period throughout the day are shown in a table below. The problem analysis rule is shown by 0309-0318 in the above table. The preprandial period, the nighttime period and the bedtime period throughout the day are shown in Table 4.

TABLE 4

| Period | Definition (h) |
|---|---|
| Nighttime | [0, 6) |
| Before breakfast | $[t_z - 1, t_z)$ |
| Before lunch | $[t_w - 1, t_w)$ |
| Before dinner | $[t_s - 1, t_s)$ |
| Before sleep | [21, 23) |

(4) Evaluation on GV and Analysis:

The blood glucose fluctuation includes an intra-day blood glucose fluctuation and an inter-day blood glucose fluctuation. Common indexes of the CGM for evaluating the GV include a standard deviation of blood glucose (SDBG), a mean amplitude of glycemic excursion (MAGE), a largest amplitude of glycemic excursion (LAGE), a coefficient of variation (CV), and a mean of daily differences (MODD).

According to the expert consensus, the intra-day blood glucose fluctuation is evaluated with a fluctuation of a median line in each of the nighttime period, the breakfast period, the lunch period, and the dinner period. Causes of the problem are tracked easily through segmented discussion. Assume that $\overline{SDBG_y}$, $\overline{LAGE_y}$, $\overline{CV_y}$ are respectively an average of the SDBG, an average of the LAGE, and an average of the CV in the nighttime period throughout the day, and $\overline{SDBG_z}$, $\overline{LAGE_z}$, $\overline{CV_z}$, $\overline{SDBG_w}$, $\overline{LAGE_w}$, $\overline{CV_w}$, and $\overline{SDBG_s}$, $\overline{LAGE_s}$, $\overline{CV_s}$ are an average of the SDBG, an average of the LAGE, and the average of the CV in the breakfast period, the lunch period and the dinner period throughout the day. The breakfast period, the lunch period and the dinner period are shown in Table 5 according to the *Chinese Clinical Guidelines for Continuous Glucose Monitoring* (2017 edition).

TABLE 5

| Period | Definition (h) |
|---|---|
| Nighttime | [0, 6) |
| Breakfast | $[t_z - 1, t_z + 3)$ |
| Lunch | $[t_w - 1, t_w + 3)$ |
| Dinner | $[t_s - 1, \min(24, t_w + 3)$ |

On the other hand, for the intra-day fluctuation, it is recommended to view an interquartile range (IQR) and an interventile range (IVR) in segments. However, the IQR and the IVR is intended to make multi-day continuous blood glucose data visual for the convenience for the doctor, so no definite thresholds are provided. Therefore, the MODD is used. Assume that MODD is an average MODD. The evaluation on the GV and the analysis rule are shown in Table 6.

TABLE 6

| Serial No. | Condition | Conclusion |
|---|---|---|
| 0401, 0403, 0405, 0407 | $\overline{SDBG_{y/z/w/s}} \geq 1.40$ or $\overline{LAGE_{y/z/w/s}} \geq 4.40$ or $\overline{CV_{y/z/w/s}} \geq 33\%$ | Large fluctuation at nighttime, breakfast or lunch or dinner |
| 0402, 0404, 0406, 0408 | $\overline{SDBG_{y/z/w/s}} < 1.40$ and $\overline{LAGE_{y/z/w/s}} < 4.40$ and $\overline{CV_{y/z/w/s}} < 33\%$ | Normal fluctuation at nighttime, breakfast or lunch or dinner |
| 0409 | $\overline{MODD}_{\geq 0.83}$ | Large inter-day blood glucose fluctuation |
| 0410 | $\overline{MODD}_{<0.83}$ | Normal inter-day blood glucose fluctuation |

(5) Evaluation on a Hyperglycemia Risk and Analysis:

The concept for designing the rule for evaluating the hyperglycemia risk is referred to the concept for designing the rule for evaluating the hypoglycemia risk in (3). Assume that the ventile is located at time $t_3$ of the hyperglycemic range. For the patients with different types of diabetes, personalized time above range (TAR) and personalized thresholds are used. The rule for evaluating the hyperglycemia risk is shown in Table 7. In addition, according to definitions of common hyperglycemic events, statistics and analysis on common types of hyperglycemic events are supplemented, as shown in Table 8. This work improves the decision efficiency of the analyst to trace specific causes of hyperglycemic regions in the AGP. The patients with different types of diabetes have different FBG control objectives and different postprandial blood glucose control objectives. Assuming that upper limits of blood glucose control ranges are respectively $h_1$ and $h_2$, the fasting hyperglycosemia and the postprandial hyperglycemia are defined by determining whether they exceed the $h_1$ and the $h_2$. According to the *Expert Consensus of AGP in Clinical Application* (2023), *Guidelines on Diagnosis and Management of Hyperglycemia in Pregnancy* (2022), and *Management Status and Response Strategies for Inpatient Blood Glucose Control in China*, Johnson et al. takes 130 mg/dL as an FBG or preprandial blood glucose threshold for the patients with type 2 diabetes to set upper limits $h_1$ and $h_2$ of blood glucose control ranges for patients with type 1 and 2 diabetes, older high-risk diabetic patients, and pregnant patients with type 1 diabetes, as shown in Table 9 below. The personalized $h_1$ and $h_2$ may also be set according to actual conditions of the patients. Whether the six hyperglycemic events occur is determined every day. Assume that numbers of days with hyperglycemic events after breakfast, lunch, and dinner are respectively $w_1$, $w_2$ and $w_3$, and numbers of days with the nocturnal insulin deficiency, the dawn phenomenon, and the Somogyi phenomenon are respectively $w_4$, $w_5$ and $w_6$.

TABLE 7

| Serial No. | Condition | Conclusion |
|---|---|---|
| 0501 | TAR < tαr and TAR2 < tαr2 and $t_3 = 0$ | Low hyperglycemia risk |
| 0502 | TAR < tαr and TAR2 < tαr2 and $t_3 > 0$ | Relatively low hyperglycemia risk |
| 0503 | TAR < tαr and TAR2 ≥ tαr2 and $t_3 > 0$ | Relatively high hyperglycemia risk |
| 0504 | TAR ≥ tαr and TAR2 < tαr2 and $t_3 > 0$ | Relatively hyperglycemia risk |
| 0505 | TAR ≥ tαr and TAR2 ≥ tαr2 and $t_3 > 0$ | Hyperglycemia risk |

TABLE 8

| Serial No. | Condition | Conclusion |
|---|---|---|
| 0506, 0507, 0508 | $W_1 > 0$, $W_2 > 0$, $W_3 > 0$ | The hyperglycemia occurs after breakfast, lunch and dinner, with the corresponding numbers of days being respectively $W_1$, $W_2$ and $W_3$ |
| 0509 | $W_4 > 0$ | The nocturnal insulin deficiency occurs, with the number of days being $W_4$ |
| 0510 | $W_5 > 0$ | The dawn phenomenon occurs, with the number of days being $W_5$ |
| 0511 | $w_6 > 0$ | The Somogyi phenomenon occurs, with the number of days being $W_6$ |

TABLE 9

| | Patients with type 1 and 2 diabetes | Older high-risk diabetic patients | Pregnant patients with type 1 diabetes |
|---|---|---|---|
| $h_1$ | 7.2 mmol/L | 7.8 mmol/L | 5.3 m1nol/L |
| $h_2$ | 10 mmol/L | 10 mmol/L | 7.8 mmol/L |

Definitions or calculation methods of special designed indexes in the rule are described as follows:

The numbers $w_1$, $w_2$, $w_3$, $w_4$, $w_5$ and $w_6$ of days with hyperglycemic events:

The $w_1$, $w_2$, $w_3$, $w_4$, $w_5$ and $w_6$ are respectively the numbers of days with the six hyperglycemic events during the monitoring period, reflecting cumulative results of daily evaluation. The daily calculation is shown in Table 10.

TABLE 10

| Hyperglycemic event | Determination method |
|---|---|
| Hyperglycemia after breakfast | There are at least two CGM data values exceeding the $h_2$ in the period $[t_z, t_z + 3)$, and the maximum fluctuation amplitude ≥2.2 mmol/L in the period $[t_z - 1, t_z + 3)$ |

TABLE 10-continued

| Hyperglycemic event | Determination method |
|---|---|
| Hyperglycemia after lunch | There are at least two CGM data values exceeding the $h_2$ in the period $[t_w, t_w+3)$, and the maximum fluctuation amplitude ≥2.2 mmol/L in the period $[t_w-1, t_w+3)$ |
| Hyperglycemia after dinner | There are at least two CGM data values exceeding the $h_2$ in the period $[t_s, \min(t_s+3, 24))$, and the maximum fluctuation amplitude ≥2.2 mmol/L in the period $[t_s-1, t_s+3)$ |
| Nocturnal insulin deficiency | There are at least two CGM data values exceeding the $h_1$ and no hypoglycemia region in the periods [0, 3] and [3, 6] |
| Dawn phenomenon | There are at least two CGM data values exceeding the $h_1$ in the period $[4, \min(t_z-1, 8)]$, no CGM data value exceeding the $h_1$ in the period [0, 3], a difference ≥1.11 mmol/L between the blood glucose and the nighttime minimum blood glucose in the period $\min(t_z-1, 8)$, and no hypoglycemia region in the period [0, 6] |
| Somogyi phenomenon | There are at least two CGM data values exceeding the $h_1$ in the period $[4, \min(t_z-1, 8)]$, and at least two CGM data values in the hypoglycemia region in the period [0, 6] |

2. Construction of an Intelligent Patient Problem Analysis Tree (1) GSP Feature Extraction First of all, for a CGM matrix $X \in R^{M \times N}$ of patients, GSP features $G \in R^{M \times 9}$ of the patients are calculated, M being a number of the patients, and N being a number of acquired blood glucose values from the patients. With the GSP features as an input, a K-means clustering algorithm is used to obtain possible clusters of the patients.

The process of the feature extraction algorithm is described as follows:

The calculation equations are as follows:

$$GSP_k = \frac{\sum_{i=1}^{N} f(x_i^p, p_k)}{N}$$

$$f(x_i^p, p_k) = \begin{cases} 1 & x_i^p = p_k \\ 0 & x_i^p \neq p_k \end{cases} \#$$

where $$x_i^p$$

denotes a blood glucose pattern of a CGM sequence at time i, $p_k$ denotes a kth blood glucose pattern of a pattern P, and has a same meaning of $GSP_k$ at a kth position, and a function $f(x_p, p_k)$ is used to label whether a symbol status at present time is the same as that at the $P_k$, counting being performed if yes, and 0 being assigned if no.

The pseudocodes of the algorithm are shown in Table 11.

TABLE 11

| The algorithm 1 is based on GSP feature extraction of domain knowledge |
|---|
| Input: CGM array matrix $X \in R^{M \times N}$, M being a number of patients, and N being a number of acquired blood glucose values from the patients; and initialize the GSP feature matrix $G \in R^{M \times 9}$ to all zero values. |
| 1. fori: 1toMdo |
| 2. forj: 1toN-1do |
| 3. Calculate a gradient of an ith patient at jth time according to $d_{i,j} = x_{i,j} - x_{i,j+1}$. |
| 4. For $\{x_{i,j}, d_{i,j}\}$, obtain a corresponding blood glucose pattern $x_{i,j}^p$ through a blood glucose conversion rule. |
| 5. Correspond a blood glucose pattern of the ith patient at the jth time to the GSP feature according to an equation $f(x_i^p, p_k) = \begin{cases} 1 x_i^p = p_k \\ 0 x_i^p \neq p_k \end{cases}$, and add 1 to a corresponding pattern in $F_i$. |
| 6. End |
| 7. End |
| 8. Normalize the feature matrix G, and divide the whole matrix G by N. |
| Output: the feature matrix G |

(2) K-Means Clustering

Before the algorithm is used, a number K of clusters is determined first. To ensure accuracy of the result, four evaluation standards are used to select the K. K=4 is taken as a final class number. The GSP features and the K value are input to the K-means clustering algorithm. Until the algorithm converges, clusters of the patients are output. According to clinical significance, the patients are classified to the following four classes, as shown in Table 12.

TABLE 12

| | Clinical significance | Adjustment strategy |
|---|---|---|
| T1 | The blood glucose control is relatively good, with more insulin secretion (IS) patterns, slight fluctuations and little hypoglycemia | Conservative treatment strategy |
| T2 | The hyperglycemic fluctuation is more evident | Accurate treatment strategy |

TABLE 12-continued

| | Clinical significance | Adjustment strategy |
|---|---|---|
| T3 | Hyperglycemia occurs in most cases, but its fluctuation is less than that of the T2 | Accurate treatment strategy |
| T4 | The blood glucose control is the best | Conservative treatment strategy |

(3) Design of the Problem Analysis Tree

Figure 3:
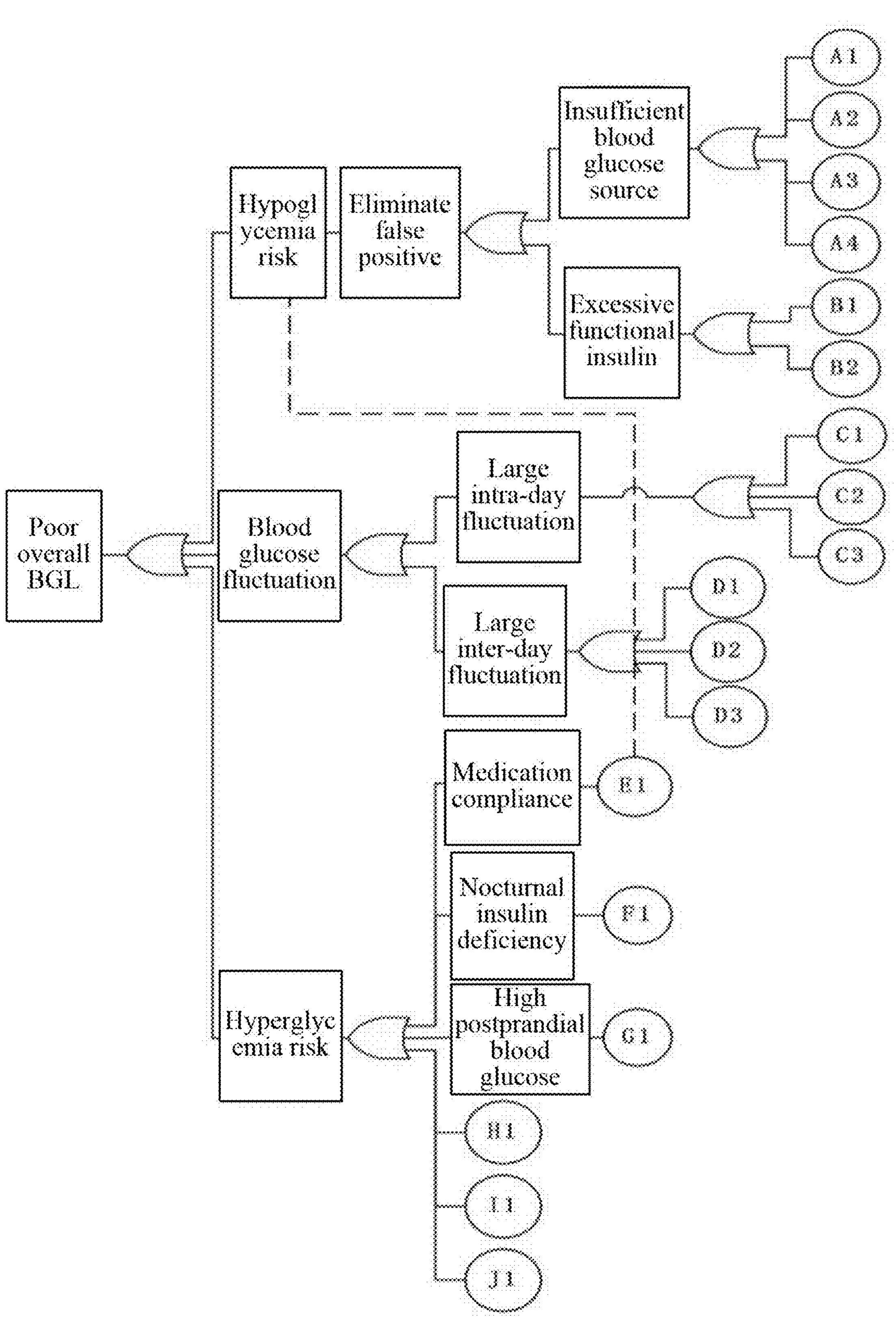
FIG. 3 is an overall schematic structural view of an intelligent patient problem analysis tree according to an embodiment of the present disclosure.

As shown in FIG. 3, to adjust the scheme, AGP interpretation and treatment on the patient need to be comprehensively considered, and the rule cannot be designed directly. With reference to the FTA method and the expert guideline, the problem analysis tree in hypoglycemia, blood glucose fluctuation and hyperglycemia of the patient is constructed.

Each branch on the problem analysis tree corresponds to one or more rules. Each rule is expanded with the expert AGP interpretation and adjustment experience according to the causes of diseases. The events, significances and corresponding adjustment schemes are shown in Table 13 below.

TABLE 13

| Event | Significance | Adjustment scheme |
|---|---|---|
| A1 | Not eating enough | Timed and measured eating is required. If the food intake is reduced, the dosage of the hypoglycemic agent is reduced correspondingly. In case of a possible delayed meal, preparations shall be made in advance (a1) |
| A2 | Excessive drinking and drinking at an empty stomach | The excessive drinking and the drinking at the empty stomach shall be avoided (a2) |
| A3 | Increase in physical activities | Appropriate exercise modes shall be selected according to the state of an illness and the physical fitness. Extra intake of carbohydrates shall be increased before the exercise (a3) |
| A4 | Other | In case of other possible induction factors (vomit, diarrhea, autonomic dysfunction, and hepatic and renal dysfunction), targeted adjustment is performed (a4) |
| B1 | Basal insulin | The basal insulin is reduced (b1) |
| B2 | Excessive mealtime insulin | The insulin at breakfast is decreased (b2-1)/the insulin at lunch is decreased (b2-2)/the insulin at dinner is decreased (b2-3) |
| C1 | Delayed bedtime | Earlier bedtime is encouraged (c1) |
| C2 | Insufficient mealtime insulin | The insulin at breakfast is increased (c2-1)/the insulin at lunch is increased (c2-2)/the insulin at dinner is increased (c2-3) |
| C3 | High carbohydrate ratio | The carbohydrate ratio at breakfast is decreased (c3-1)/the carbohydrate ratio at lunch is decreased (c3-2)/the carbohydrate ratio at dinner is decreased (c3-3) |
| D1, D2, D3 | Irregular sleep/meal/exercise | Regular sleep (d1)/meal (d2)/exercise (d3) is required |
| E1 | Fear of hypoglycemia | Psychological support is provided for the patients to prevent the fear of hypoglycemia (e1) |
| F1 | Insufficient basal insulin | The basal insulin is increased (f1) |
| G1 | Insufficient mealtime insulin | The insulin at breakfast is increased (g1-1)/the insulin at lunch is increased (g1-2)/the insulin at dinner is increased (g1-3) |
| H1, I1, J1 | Dawn phenomenon, Somogyi phenomenon, and other hyperglycemic events | Adjustment is made according to a specific condition |
| K1, K2 | Insulin dosage adjustment suggestion/conservative insulin adjustment suggestion | Accurate dosage is output according to fuzzy inference/the dosage is decreased or increased appropriately according to a BGL |

In combination with the above table and the AGP interpretation, conditions and conclusions of the rule are obtained, as shown in Table 14, Table 15 and Table 16 below. The conclusions of the rule are correspondingly adjusted according to the schemes in the above table. The conditions of the rule are correspondingly manifested by the indexes of the events. Assume that medians of fluctuation ranges at breakfast, lunch and dinner are respectively $LAGE_z$, $LAGE_w$ and $LAGE_s$. Assume that at nighttime, before lunch, before dinner, and before sleep, proportions of days with hypoglycemia are $m_{11}$, $m_{13}$, $m_{14}$ and mis, proportions of days with elevated blood glucose are $m_{21}$, $m_{23}$, $m_{24}$ and $m_{25}$, and proportions of days with hyperglycemia are $m_{31}$, $m_{33}$, $m_{34}$ and $m_{35}$. In the rule, the hypoglycemia is adjusted preferentially. Accordingly, the insulin adjustment rule is 0605-0608, 0702-0707 and 0804-0808.

TABLE 14

| Serial No. | Condition | Conclusion |
|---|---|---|
| 0601 | $n_{23}$ > $Oorn_{24}$ > $Oorn_{25}$ > 0 | al |
| 0602, 0603 | $n_{22}$ > $Oorn_{23}$ > $Oorn_{24}$ > $Oorn_{25}$ > 0 | a2, a3 |
| 0604 | $t_2$ > 0 | a4 |
| 0605-0608 | $m_{11}$ > 0.2 or $m_{13}$ > 0.2 or $m_{14}$ > 0.2 or $m_{15}$ > 0.2 | blor b2-lor b2-2or b2-3 |
| 0609 | $t_2$ > 6 | el |

TABLE 15

| Serial No. | Condition | Conclusion |
|---|---|---|
| 0701 | $\overline{SDBG_y} \geq 1.40$ or $\overline{LAGE_y} \geq 4.40$or$\overline{CV_y} \geq 33\%$ | cl |
| 0702, 0703, 0704 | $\overline{SDBG_z} \geq 1.40$ or $\overline{LAGE_{z/w/s}} \geq 4.40$ or $\overline{CV_{z/w/s}} \geq 33\%$ and $m_{23/24/25}$ > 0.4 and $m_{13/14/15}$ = 0 | c2-1/c2-2/ c2-3 |
| 0705, 0706, 0707 | $\overline{SDBG_{z/w/s}} \geq 1.40$ or $\overline{LAGE_{z/w/s}} \geq 4.40$ or $\overline{CV_{z/w/s}} \geq 33\%$ | c3-1/c3-2 c3-3 |
| 0708 | $\overline{MODD} \geq 0.83$ | dl, d2, d3 |

TABLE 16

| Serial No. | Condition | Conclusion |
|---|---|---|
| 0802 | $w_4$ > 0 and $m_{21}$ > 0.4 and $m_{11}$ = 0 | f1 |
| 0804, 0806, 0808 | $w_1$ > 0 and $m_{23/24/25}$ > 0.4 and $m_{13/14/15}$ = 0 and not(c2 − 1/2/3) and $LAGE_{z/w/s} \geq$ 2.2 and $m_{31}$ < 0.4 | g1-1/g1-2/g1-3 |
| 0812 | $t_3$ > 0 | Hyperglycemia caused by other reasons is viewed, and adjustment is made according to a specific condition |

(4) Intelligent Adjustment Design of the Problem Analysis Tree

Figure 4A:
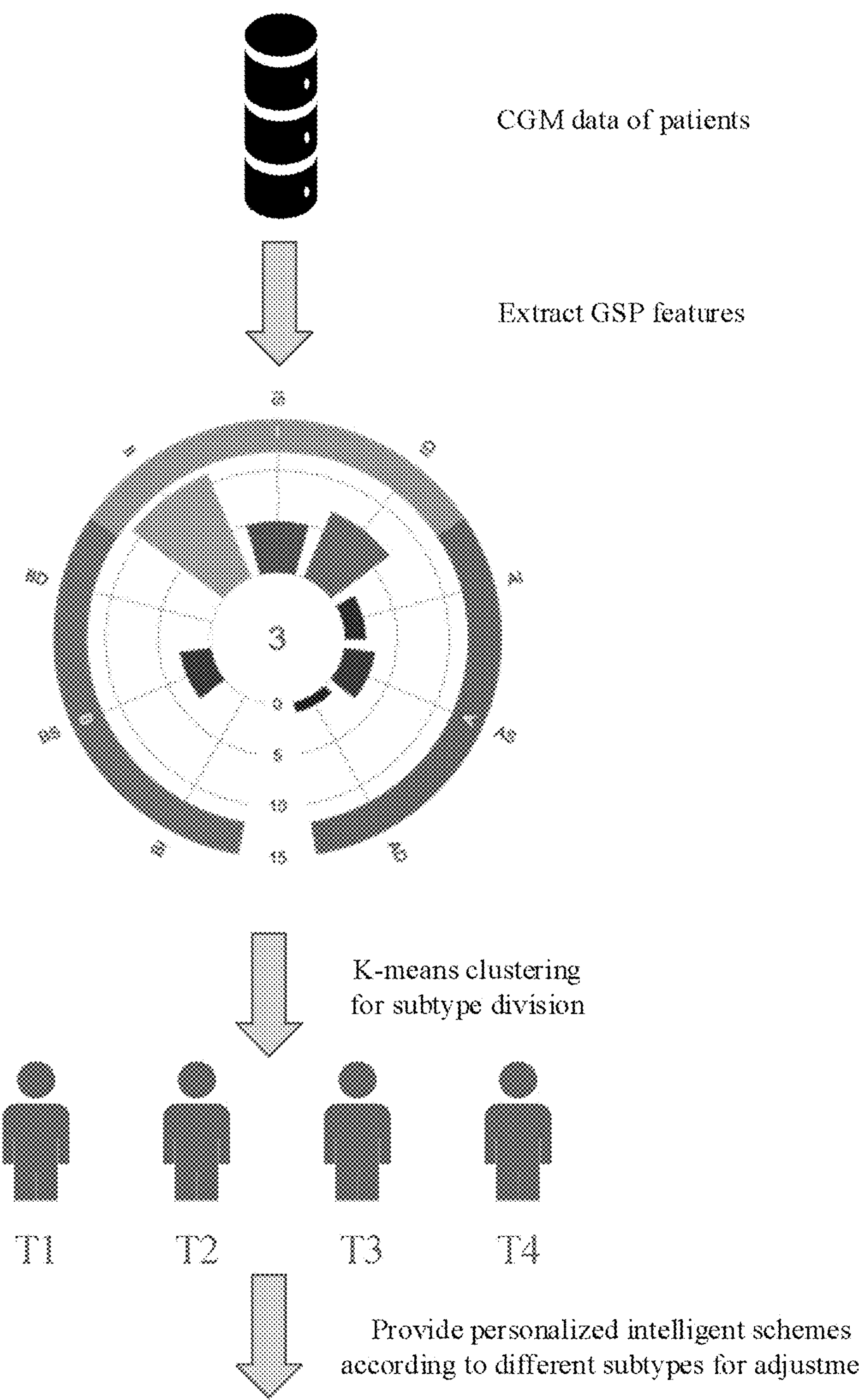
FIGS. 4A-4B are overall schematic construction flowcharts of an intelligent patient problem analysis tree according to an embodiment of the present disclosure, where
Figure 4B:
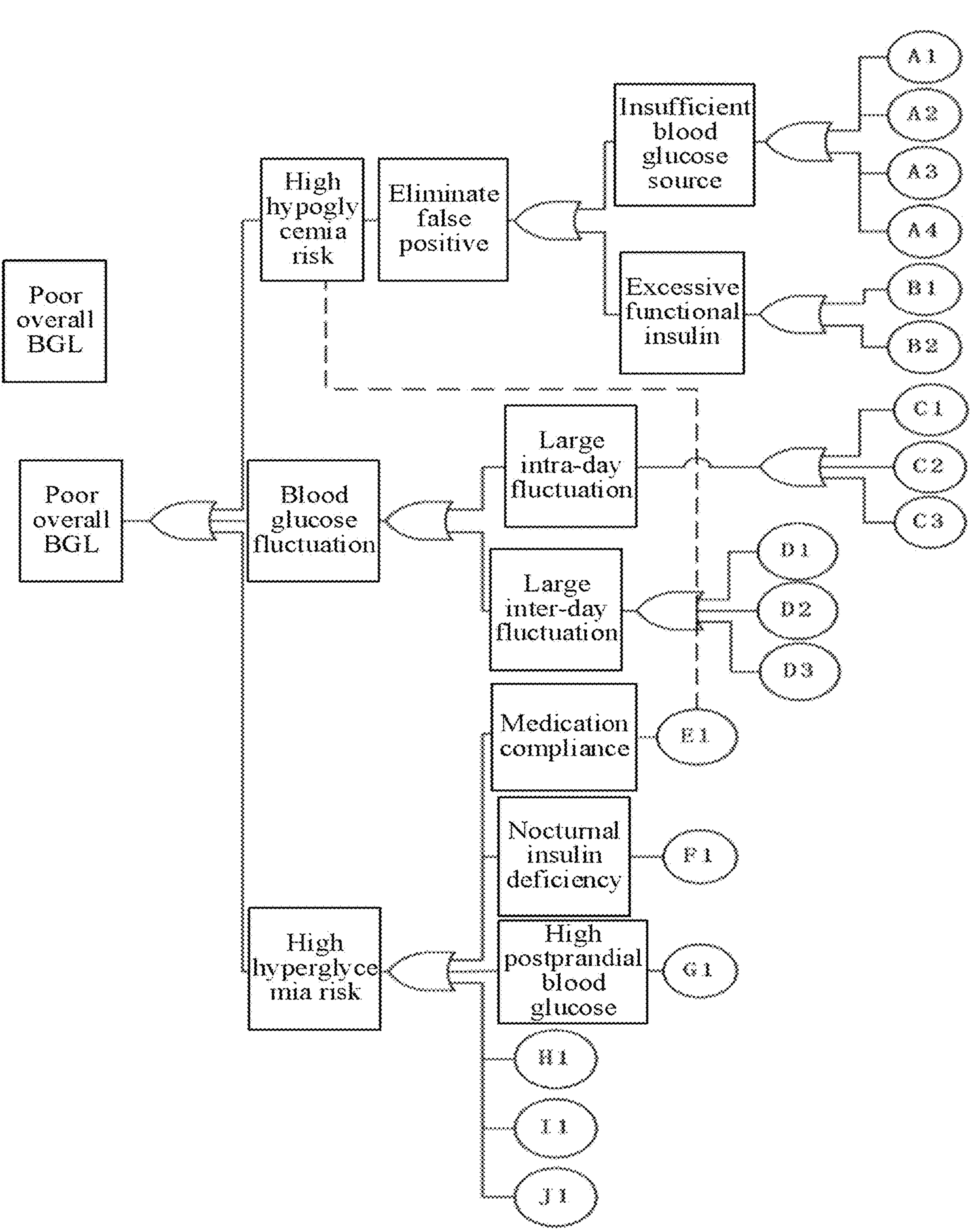
Figure 5:
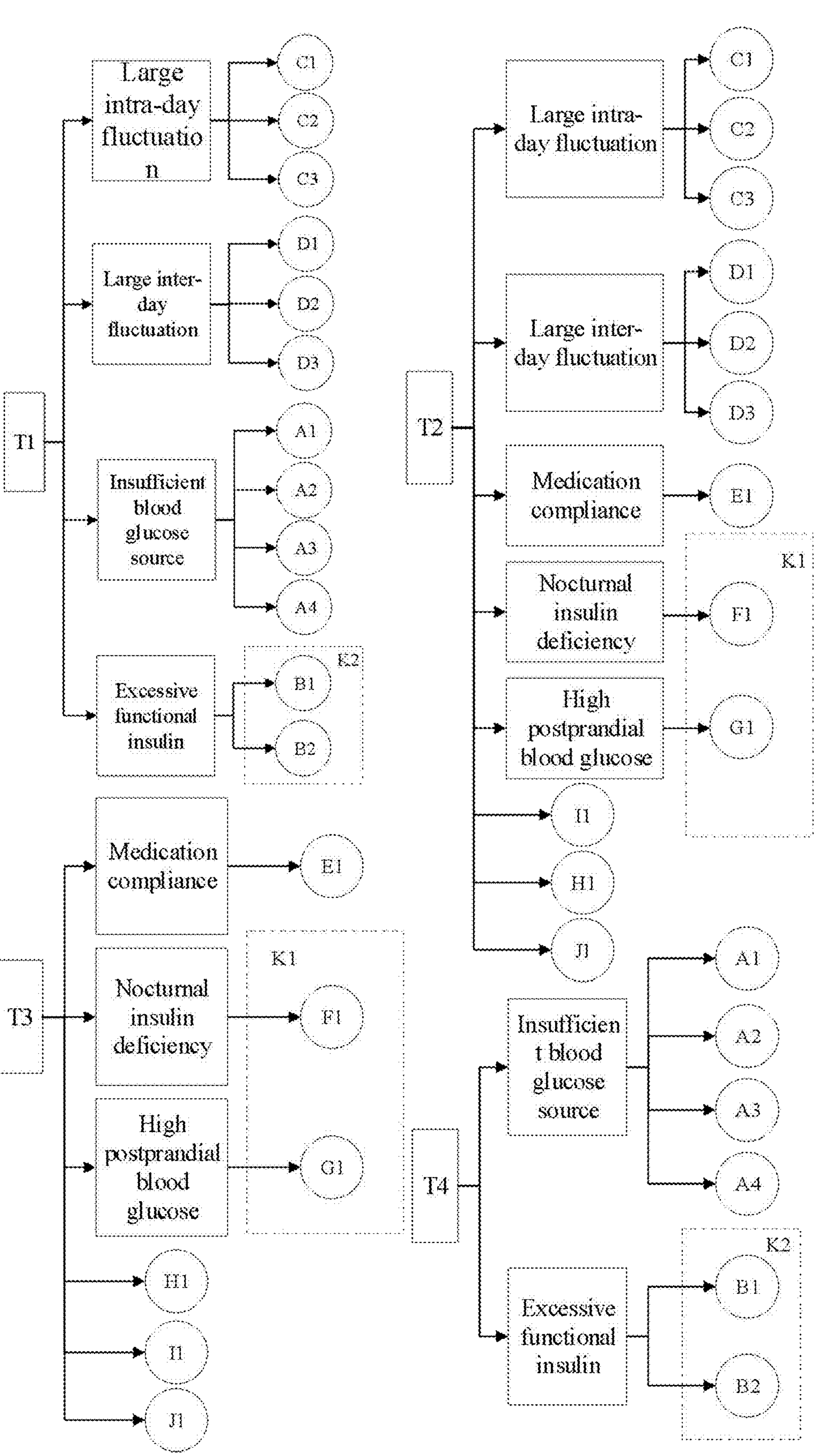
FIG. 5 is a schematic view of structures corresponding to four subtype groups in an intelligent patient problem analysis tree according to an embodiment of the present disclosure.
Figures 6A, 6B:
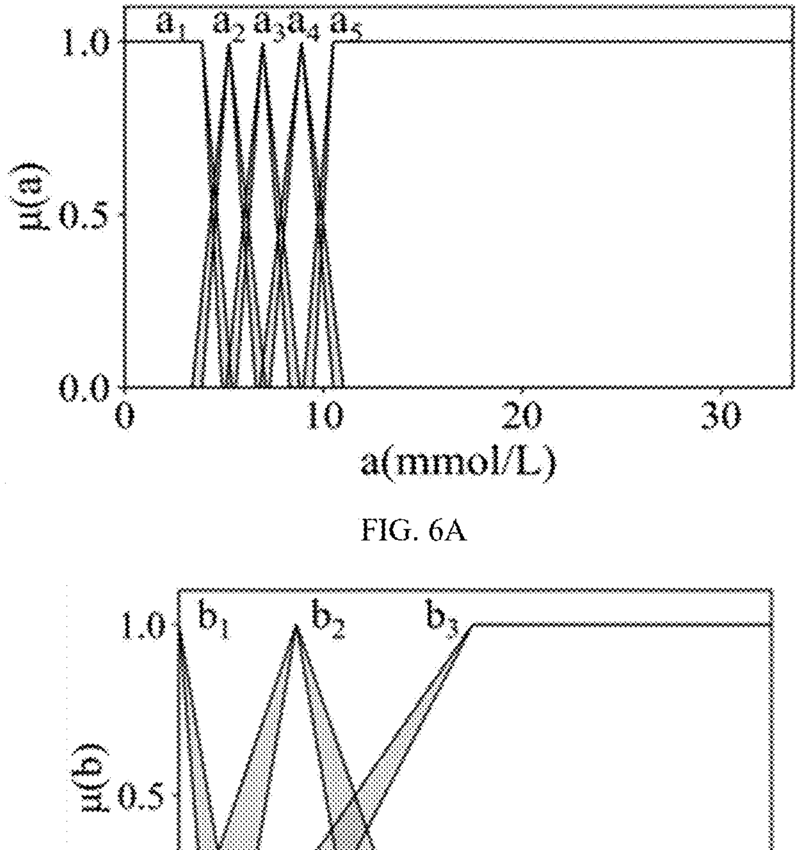
FIGS. 6A-6D illustrate membership functions of four input indexes in a basal insulin dosage adjustment fuzzy expert system according to an embodiment of the present disclosure.
Figures 6C, 6D:
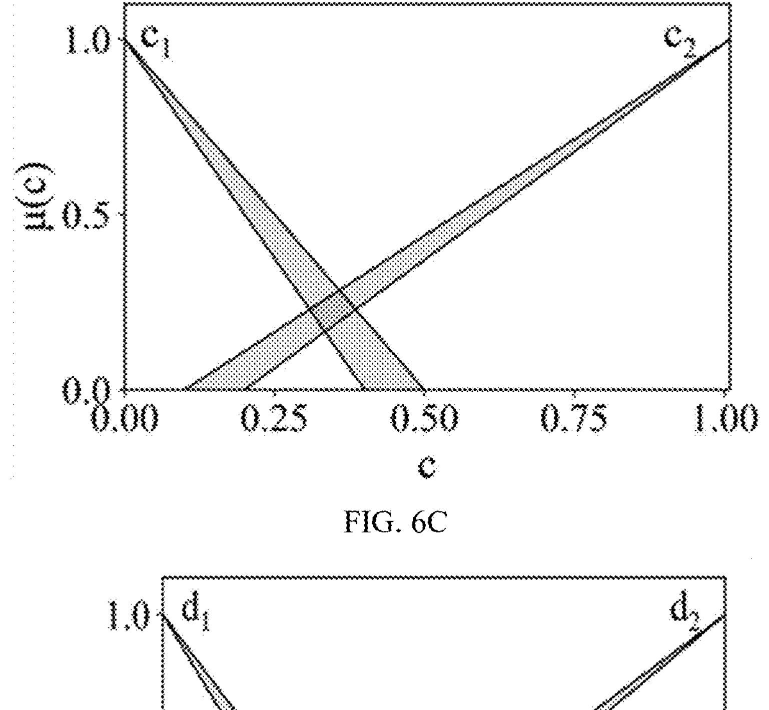

The established patient problem analysis tree can provide the intelligent decision support for the patients, but cannot provide targeted and personalized suggestions. Hence, the present disclosure adopts the clustering method. According to the GSP features, the patients are divided into four subtype groups T1, T2, T3 and T4 by using the K-means clustering algorithm. In this way, the expert system can intelligently adjust the node of the problem tree according to the groups of the patients, providing more personalized and targeted intelligent decision suggestions. The specific analysis flowchart is shown in FIGS. 4A-4B. The specific analysis tree for each group is shown in FIG. 5.

3. Construction of "Basal+Mealtime" Insulin Dosage Adjustment Methods Based on an Interval Type-2 Fuzzy Expert System (1) Basal Insulin Dosage Adjustment Fuzzy Expert System The index selection and fuzzification are shown in Table 17 and Table 18:

TABLE 17

| FBG (mmol/L) | Basal insulin adjusted dosage (IU) |
|---|---|
| <4.4 | −2 |
| 4.4-6.1 | 0 |
| 6.2-7.8 | +2 |
| 7.9-10.0 | +4 |
| >10 | +6 |

TABLE 18

| FBG condition | Basal insulin adjusted dosage (IU) |
|---|---|
| Two readings or more <70 mg/dL | −4 |
| One reading <70 mg/dL | 0 |
| No reading <70 mg/dL and more than three readings >130 mg/dL | +2 |
| No reading <70 mg/dL and more than three readings >180 mg/dL | +4 |
| Others | 0 |

In combination with the above two basal insulin dosage adjustment rules, a multi-day FBG median a, a proportion b of days with nocturnal blood glucose in a hypoglycemic range, a proportion c of days with nocturnal blood glucose elevated, and a proportion d of days with nocturnal blood glucose in a hyperglycemic range are taken as system input indexes (there are at least two CGM data values in a set range in the period). Membership functions of the above indexes are shown in FIGS. 6A-6D. Assume that the basal insulin adjusted dosage e serves as a system output.

To reduce the overall calculation complexity, a membership function for each index is established with an interval type-2 fuzzy set dominated by a triangle and followed by a trapezoid. In the domain of discourse, a includes five fuzzy sets, namely low $a_1$, medium $a_2$, slightly high $a_3$, slight high $a_4$, and very high $a_5$. To set reference indexes for the patients with type 1 and type 2 diabetes, the membership function is as follows:

$$a_1 = \int_{a\in(0,3.9]}\int_{u=1}\frac{1}{(a,u)} + \int_{a\in(3.9,4.9]}\int_{u\in[-0.67a+3.62,-1a+4.9]}\frac{1}{(a,u)} + \int_{a\in(4.9,5.4]}\int_{u\in[0,-1a+4.9]}\frac{1}{(a,u)}$$

$$a_2 = \int_{a\in(3.4,3.9]}\int_{u\in[0,0.54a-1.84]}\frac{1}{(a,u)} + \int_{a\in(3.9,5.25]}\int_{u\in[0.7a-3.89,0.54a-5.18]}\frac{1}{(a,u)} + \int_{a\in(5.25,6.6]}\int_{u\in[-0.7a+4.89,-0.54a+3.83]}\frac{1}{(a,u)} + \int_{a\in(6.6,7.1]}\int_{u\in[0,-0.54a+3.83]}\frac{1}{(a,u)}$$

$$a_3 = \int_{a\in(5.1,5.6]}\int_{u\in[0,0.54a-2.75]}\frac{1}{(a,u)} + \int_{a\in(5.6,6.95]}\int_{u\in[0.74a-4.14,0.54a-2.75]}\frac{1}{(a,u)} + \int_{a\in(6.95,8.3]}\int_{u\in[-0.74a+6.14,-0.54a+4.75]}\frac{1}{(a,u)} + \int_{a\in(8.3,8.8]}\int_{u\in(0,-0.54a+4.75]}\frac{1}{(a,u)}$$

$$a_4 = \int_{a\in(6.8,7.3]}\int_{u\in[0,0.48a-3.26]}\frac{1}{(a,u)} + \int_{a\in(7.3,8.9]}\int_{u\in[0.63a-4.60,0.48a-3.26]}\frac{1}{(a,u)} +$$

-continued $$\int_{a\in(8.9,10.5]}\int_{u\in[-0.63a+6.62,-0.48a+5.28]}\frac{1}{(a,\ u)}+\int_{a\in(10.5,11.0]}\int_{u\in[0,-0.48a+5.28]}\frac{1}{(a,\ u)}$$

$$a_5=\int_{a\in(9.0,9.5]}\int_{u\in[0,0.67a-6.03]}\frac{1}{(a,\ u)}+\int_{a\in(9.5,10.5]}\int_{u\in[1-9.5,0.67a-6.03]}\frac{1}{(a,\ u)}+\int_{a\in(10.5,33.3]}\int_{u=1}\frac{1}{(a,\ u)}$$

For different types of patients, parameters of the membership function of the fuzzy set of $x_1$ in the domain of discourse are shown in Table 19:

For c and d, there are two fuzzy sets, namely low $c_1$, $d_1$ and high $c_2$, $d_2$ in the domain of discourse. The membership function is as follows:

$$c_1=\int_{c\in(0,0.4]}\int_{u\in[-2.5c+1,-2c+1]}\frac{1}{(c,\ u)}+\int_{c\in(0.4,0.5]}\int_{u\in[0,-2c+1]}\frac{1}{(c,\ u)} \quad (0.1)$$

$$c_2=\int_{c\in(0.1,0.2]}\int_{u\in[0,1.11c-0.11]}\frac{1}{(c,\ u)}+\int_{\in(0.2,1]}\int_{u\in[1.25c-0.25,1.11c-0.11]}\frac{1}{(c,\ u)}$$

$$d_1=\int_{d\in(0,0.4]}\int_{u\in[-2.5d+1,-2d+1]}\frac{1}{(d,\ u)}+\int_{d\in(0.4,0.5]}\int_{u\in[0,-2d+1]}\frac{1}{(d,\ u)}$$

TABLE 19

| | | Patients with type 1 and 2 diabetes | Older high-risk diabetic patients | Pregnant patients with type 1 diabetes |
|---|---|---|---|---|
| $a_1$ | Upper membership grade | [0, 0, 3.9, 5.4] | [0, 0, 3.9, 5.4] | [0, 0, 3.5, 5.0] |
| | Lower membership grade | [0, 0, 3.9, 4.9] | [0, 0, 3.9, 4.9] | [0, 0, 3.5, 4.5] |
| $a_2$ | Upper membership grade | [3.4, 5.25, 7.1] | [3.4, 6.1, 8.8] | [3.0, 4.5, 6.0] |
| | Lower membership grade | [3.9, 5.25, 6.6] | [3.9, 6.1, 8.3] | [3.5, 4.5, 5.5] |
| $a_3$ | Upper membership grade | [5.1, 6.95, 8.8] | [6.8, 8.9, 11.0] | [4.0, 5.55, 7.1] |
| | Lower membership grade | [5.6, 6.95, 8.3] | [7.3, 8.9, 10.5] | [4.5, 5.55, 6.6] |
| $a_4$ | Upper membership grade | [6.8, 8.9, 11.0] | [[9.0, 11.95, 14.9] | [5.1, 6.95, 8.8] |
| | Lower membership grade | [7.3, 8.9, 10.5] | [9.5, 11.95, 14.4] | [5.6, 6.95, 8.3] |
| $a_5$ | Upper membership grade | [9, 10.5, 33.3, 33.3] | [12.9, 14.4, 33.3, 33.3] | [6.8, 8.3, 33.3, 33.3] |
| | Lower membership grade | [9.5, 10.5, 33.3, 33.3] | [13.4, 14.4, 33.3,3 3.3] | [7.3, 8.3, 33.3, 33.3] |

In the domain of discourse, b includes three fuzzy sets, namely low $b_1$, medium $b_2$, and high $b_3$. The membership function is as follows:

$$b_1=\int_{b\in(0,0.05]}\int_{u\in[-20b+1,-10b+1]}\frac{1}{(b,\ u)}+\int_{b\in(0.05,0.1]}\int_{u\in[0,-10b+1]}\frac{1}{(b,\ u)}$$

$$b_2=\int_{b\in(0,0.01]}\int_{u\in[0,5b]}\frac{1}{(b,\ u)}+\int_{b\in(0.1,0.2]}\int_{u\in[10b-1,5b]}\frac{1}{(b,\ u)}+\int_{b\in(0.2,0.3]}\int_{u\in[-10b+3,-5b+2]}\frac{1}{(b,\ u)}+\int_{b\in(0.3,0.4]}\int_{u\in[0,-5b+2]}\frac{1}{(b,\ u)}$$

$$b_3=\int_{b\in(0.1,0.2]}\int_{u\in[0,2.5b-0.25]}\frac{1}{(b,\ u)}+\int_{b\in(0.2,0.5]}\int_{u\in[3.33b-0.66,2.5b-0.25]}\frac{1}{(b,\ u)}+\int_{b\in(0.5,1]}\int_{u=1}\frac{1}{(b,\ u)}$$

-continued $$d_2=\int_{d\in(0.1,0.2]}\int_{u\in[0,1.11d-0.11]}\frac{1}{(d,\ u)}+\int_{d\in(0.2,1]}\int_{u\in[1.25d-0.25,1.11d-0.11]}\frac{1}{(d,\ u)}$$

Figure 7:
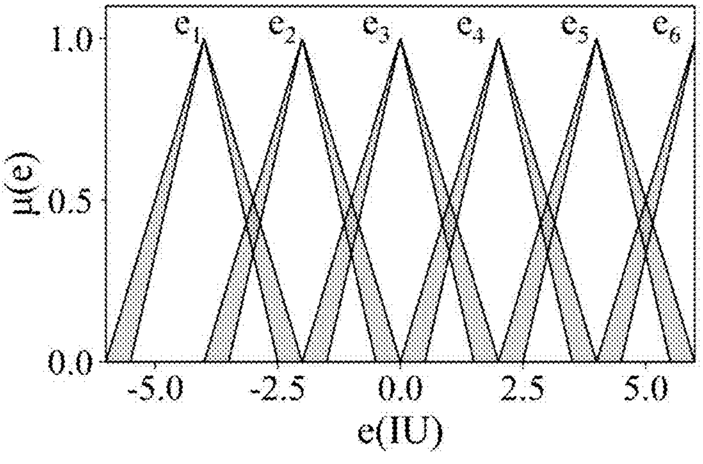
FIG. 7 illustrates a membership function of a basal insulin adjusted dosage in a basal insulin dosage adjustment fuzzy expert system according to an embodiment of the present disclosure.

In the domain of discourse, the output e includes six fuzzy sets, namely moderate decrease $e_1$, slight decrease $e_2$, no change $e_3$, slight increase $e_4$, moderate increase $e_5$, and significant increase $e_6$. The membership function is shown in FIG. 7. The membership function is as follows:

$$e_1=\int_{e\in(-6,-5.5]}\int_{u\in[0,0.5e+3]}\frac{1}{(e,\ u)}+\int_{e\in(-5.5,-4]}\int_{u\in[0.67e+3.69,0.5e+3]}\frac{1}{(e,\ u)}+\int_{e\in(-4,-2.5]}\int_{u\in[-0.67e-1.68,-0.5e-1]}\frac{1}{(e,\ u)}+\int_{\in(-2.5,-2[}\int_{u\in[0,-0.5e-1]}\frac{1}{(e,\ u)}$$

$$e_2=\int_{e\in(-4,-3.5]}\int_{u\in[0,0.5e+2]}\frac{1}{(e,\ u)}+\int_{e\in(-3.5,-2]}\int_{u\in[0.67e+2.35,0.5e+2]}\frac{1}{(e,\ u)}+$$

-continued $$\int_{e\in(-2,-0.5]}\int_{u\in[-0.67e-0.34,-0.5e]}\frac{1}{(e,u)}+\int_{e\in(-0.5,0]}\int_{u\in[0,-0.5e]}\frac{1}{(e,u)}$$

$$e_3=\int_{e\in(-2,-1.5]}\int_{u\in[0,0.5e+1]}\frac{1}{(e,u)}+\int_{\in(-1.5,0]}\int_{u\in[0.67e+1,0.5e+1]}\frac{1}{(e,u)}+\int_{e\in(0,1.5]}\int_{u\in[-0.67e+1,-0.5e+1]}\frac{1}{(e,u)}+\int_{e\in(1.5,2]}\int_{u\in[0,-0.5e+1]}\frac{1}{(e,u)}$$

$$e_4=\int_{e\in(0,0.5]}\int_{u\in[0,0.5e]}\frac{1}{(e,u)}+\int_{e\in(0.5,2]}\int_{u\in[0.67e-0.33,0.5e]}\frac{1}{(e,u)}+\int_{e\in(2,3.5]}\int_{u\in[-0.67e+2.35,-0.5e+2]}\frac{1}{(e,u)}+\int_{e\in(3.5,4]}\int_{u\in[0,0.5e+2]}\frac{1}{(e,u)}$$

$$e_5=\int_{e\in(2,2.5]}\int_{u\in[0,0.5e-1]}\frac{1}{(e,u)}+\int_{e\in(2.5,4]}\int_{u\in[0.67e-1.67,0.5e-1]}\frac{1}{(e,u)}+\int_{e\in(4,5.5]}\int_{u\in[-0.67e+3.68,-0.5e+3]}\frac{1}{(e,u)}+\int_{\in(5.5,6]}\int_{u\in[0,-0.5e+3]}\frac{1}{(e,u)}$$

$$e_6=\int_{e\in(4,4.5]}\int_{u\in[0,0.5e-2]}\frac{1}{(e,u)}+\int_{\in(-4.5,6]}\int_{u\in[0.67e-3,0.5e-2]}\frac{1}{(e,u)}$$

Rule Design:

With a fuzzy logic, a rule is formulated for dosage adjustment on basal insulin of a diabetic patient. The rule is formulated preferentially according to probabilities of hyperglycemia and hypoglycemia at night. Upon this, the rule is formulated for the dosage adjustment according to the FBG median over multiple days.

(2) Mealtime Insulin Dosage Adjustment Fuzzy Expert System

The index selection and fuzzification are shown in Table 20 and Table 21:

TABLE 20

| Difference between 2-h postprandial blood glucose and preprandial blood glucose | Mealtime insulin adjusted dosage (IU) |
|---|---|
| <1.7 mmol/L | −1-−4 |
| >3.3 mmol/L | 2-4 |

TABLE 21

| Next preprandial/pre-sleep blood glucose | Mealtime insulin adjusted dosage (IU) |
|---|---|
| Two readings or more <70 mg/dL | −2 |
| One reading <70 mg/dL | 0 |
| No reading <70 mg/dL and more than three readings >130 mg/dL | +2 |
| Others | 0 |

Figures 8A, 8B:
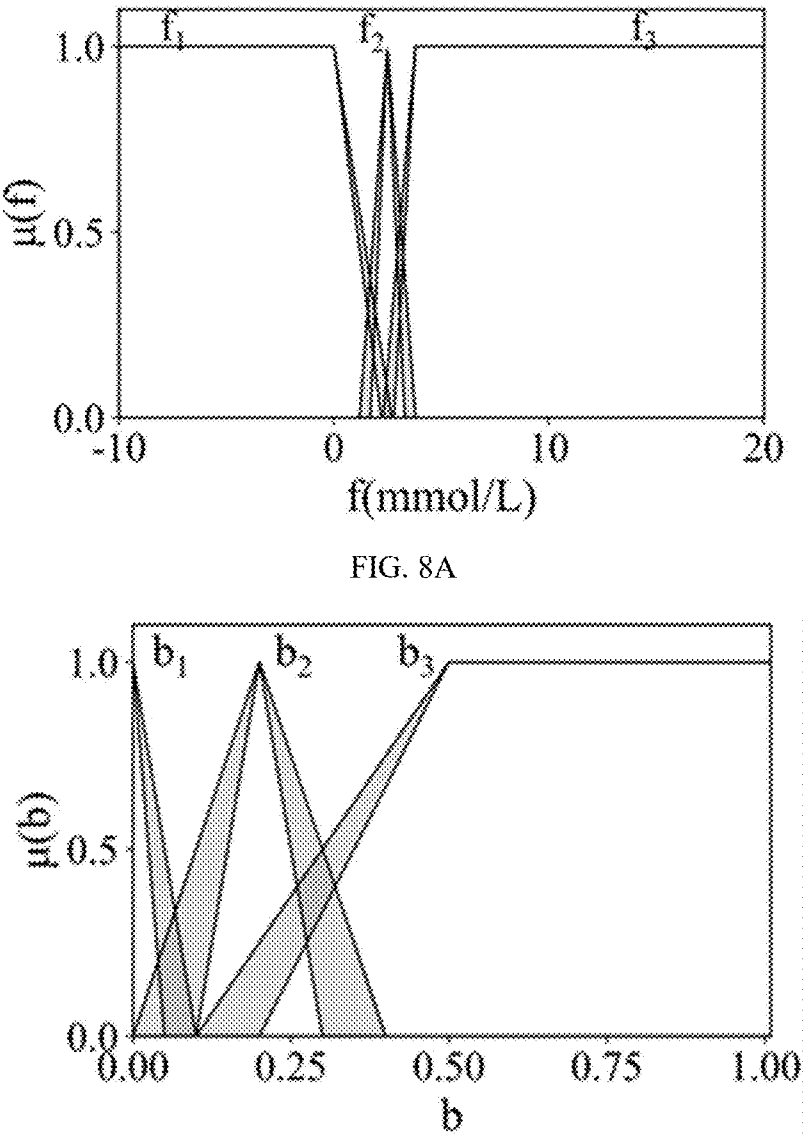
FIGS. 8A-8C illustrate membership functions of three input indexes in a mealtime insulin dosage adjustment fuzzy expert system according to an embodiment of the present disclosure.
Figures 8C, 9:
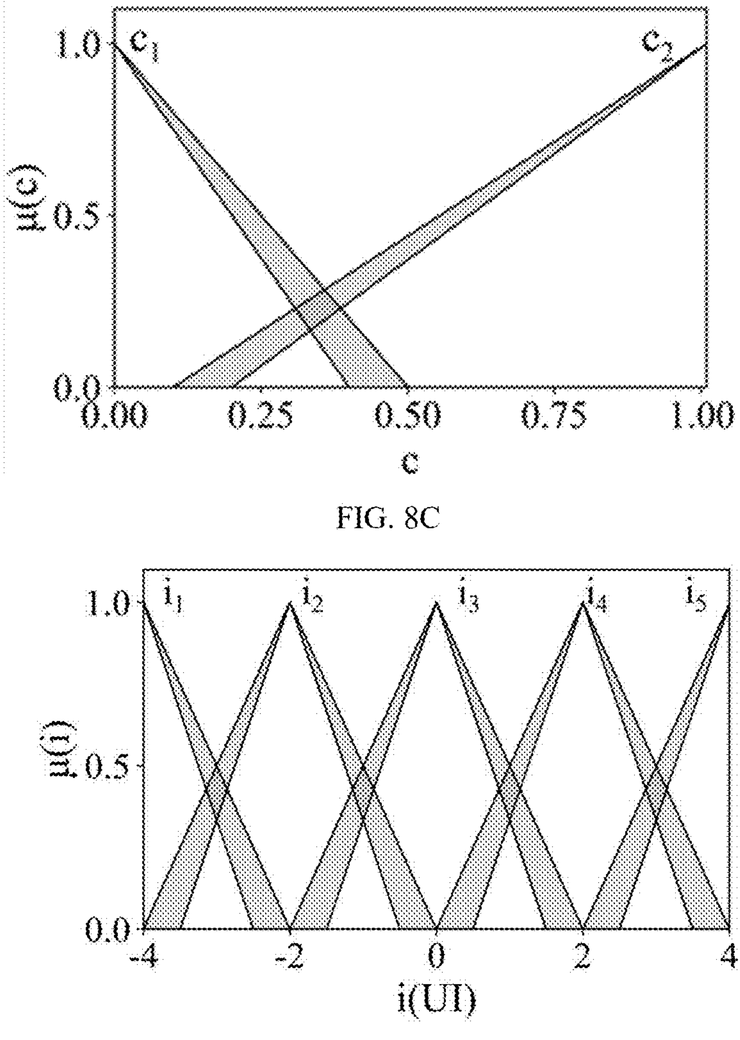
FIG. 9 illustrates a membership function of a mealtime insulin adjusted dosage in a mealtime insulin dosage adjustment fuzzy expert system according to an embodiment of the present disclosure.

In combination with a mealtime insulin adjustment rules in the above two tables, a median f for differences between 2–h postprandial blood glucose and preprandial blood glucose over multiple days, a proportion g of days with next preprandial (/pre-sleep) blood glucose in the hypoglycemic range, and a proportion h of days with next preprandial (/pre-sleep) blood glucose in an FBG elevated range (it is considered that the event exists if there are more than two CGM data in the fixed range during this period) are taken as system input indexes. Membership functions of the indexes are shown in FIGS. 8A-8C. Assume that the mealtime insulin adjusted dosage i serves as a system output.

The design concept of the membership function is the same as that of the dosage adjustment on the basic insulin. In the domain of discourse, f includes three fuzzy sets, namely low $f_1$, medium $f_2$, and high $f_3$. The membership function is as follows:

$$f_1=\int_{f\in(-\infty,0]}\int_{u=1}\frac{1}{(f,u)}+\int_{f\in(0,2.2]}\int_{u\in[-0.46f+1,-0.37f+1]}\frac{1}{(f,u)}+\int_{f\in(2.2,2.7]}\int_{u\in[0,-0.37f+1]}\frac{1}{(f,u)}$$

$$f_2=\int_{f\in(1.2,1.7]}\int_{u\in[0,0.77f-0.92]}\frac{1}{(f,u)}+\int_{f\in(1.7,2.5]}\int_{u\in[1.35f-2.13,0.77f-0.92]}\frac{1}{(f,u)}+\int_{f\in(2.5,3.3]}\int_{u\in[-1.25f+4.13,-0.77f+2.92]}\frac{1}{(f,u)}+\int_{f\in(3.3,3.8]}\int_{u\in[0,-0.77f+2.92]}\frac{1}{(f,u)}$$

$$f_3=\int_{f\in(2.3,2.8]}\int_{u\in[0,0.67f-1.54]}\frac{1}{(f,u)}+\int_{f\in(2.8,3.8]}\int_{u\in[f-2.8,0.67f-1.54]}\frac{1}{(f,u)}+\int_{f\in(3.8,+\infty)}\int_{u=1}\frac{1}{(f,u)}$$

Same as b, g includes three fuzzy sets in the domain of discourse, namely low $g_1$, medium $g_2$, and high $g_3$. Same as c, h includes two fuzzy sets in the domain of discourse, namely low $h_1$ and high $h_2$.

In the domain of discourse, the i includes five fuzzy sets, namely moderate decrease $i_1$, slight decrease $i_2$, no change $i_3$, slight increase $i_4$, and moderate increase $i_5$. The membership function is shown in FIG. 9. The membership function is as follows:

$$i_1=\int_{i\in(-4,-2.5]}\int_{u\in[-0.67i-1.68,-0.5i-1]}\frac{1}{(i,u)}+\int_{i\in(-2.5,-2]}\int_{u\in[0,-0.5i-1]}\frac{1}{(i,u)}$$

$$i_2=\int_{i\in(-4,-3.5]}\int_{u\in[0,0.5i+2]}\frac{1}{(i,u)}+\int_{i\in(-3.5,-2]}\int_{u\in[0.67i+2.35,0.5i+2]}\frac{1}{(i,u)}+\int_{i\in(-2,-0.5]}\int_{u\in[-0.67i-0.34,-0.5i]}\frac{1}{(i,u)}+\int_{i\in(-0.5,0]}\int_{u\in[0,-0.5i]}\frac{1}{(i,u)}$$

$$i_3=\int_{i\in(-2,-1.5]}\int_{u\in[0,0.5i+1]}\frac{1}{(i,u)}+\int_{i\in(-1.5,0]}\int_{u\in[0.67i+1,0.5i+1]}\frac{1}{(i,u)}+\int_{i\in(0,1.5]}\int_{u\in[-0.67i+1,-0.5i+1]}\frac{1}{(i,u)}+\int_{i\in(1.5,2]}\int_{u\in[0,-0.5i+1]}\frac{1}{(i,u)}$$

$$i_4=\int_{i\in(0,0.5]}\int_{u\in[0,0.5i]}\frac{1}{(i,u)}+\int_{i\in(0.5,2]}\int_{u\in[0.67i-0.33,0.5i]}\frac{1}{(i,u)}+\int_{i\in(2,3.5]}\int_{u\in[-0.67i+2.35,-0.5i+2]}\frac{1}{(i,u)}+\int_{i\in(3.5,4]}\int_{u\in[0,0.5i+2]}\frac{1}{(i,u)}$$

$$i_5=\int_{i\in(2,2.5]}\int_{u\in[0,0.5i-1]}\frac{1}{(i,u)}+\int_{i\in(2.5,4]}\int_{u\in[0.67i-1.67,0.5i-1]}\frac{1}{(i,u)}$$

Rule Design:

With a fuzzy logic, a rule for dosage adjustment on mealtime insulin dosage of the diabetic patient is formulated. The rule is formulated preferentially according to probabilities of next preprandial (/pre-sleep) hyperglycemia and hypoglycemia. Upon this, the rule for dosage adjustment is formulated according to the median for differences between 2–h postprandial blood glucose and preprandial blood glucose over multiple days.

(3) Incremental Learning of the Membership Function of the Rule Consequent

The above insulin dosage adjustment fuzzy inference system can provide general safety suggestions for a multi-day continuous blood glucose monitoring condition of the patient. With repeated periodic adjustment, parameters of the fuzzy inference system can be adjusted according to a blood glucose improved condition of the patient. Here, a simple incremental learning is used to adjust parameters of the membership function of the rule consequent.

If an insulin adjustment suggestions of the fuzzy inference system is adopted by the patient in a previous period to adjust basal insulin α IU (including plus and minus symbols), and mealtime insulin β IU (for multiple meals, the adjustment rule is the same; and herein, the concept of the mealtime insulin is used), suggestions of the original fuzzy inference system are used in this period to adjust the basal insulin λ IU and the mealtime insulin γ IU. It may be understood that in the previous periodic adjustment, deviations are λ and γ respectively. Accordingly, the parameters of the membership function of the rule consequent of the fuzzy inference system are adjusted. To ensure the safety, the maximum adjustment range of the parameter is set as 1. Assume that when $e_1$, $e_2$, $e_4$, $e_5$ and $e_6$ in the membership function of the basal insulin adjusted dosage have a membership degree of m, corresponding values in the domain of discourse are respectively $e_{1m}$, $e_{2m}$, $e_{4m}$, $e_{5m}$ and $c_{6m}$, and when $i_1$, $i_2$, $i_4$ and $i_5$ in the membership function of the mealtime insulin adjusted dosage have a membership degree of m, corresponding values in the domain of discourse are respectively $i_{1m}$, $i_{2m}$, $i_{4m}$ and $i_{5m}$. The parameters are updated by:

$$e_{nm} = \begin{cases} e_{nm} - \min\left(1, \frac{\lambda}{\alpha}|\alpha|\right), & n = 1, 2 \\ e_{nm} + \min\left(1, \frac{\lambda}{\alpha}|\alpha|\right), & n = 4, 5, 6 \end{cases}$$

$$i_{nm} = \begin{cases} i_{nm} - \min\left(1, \frac{\gamma}{\beta}|\beta|\right), & n = 1, 2 \\ i_{nm} + \min\left(1, \frac{\gamma}{\beta}|\beta|\right), & n = 4, 5 \end{cases}$$

That is, membership functions of some fuzzy sets of the rule consequent are moved overall according to an output of the original inference system. The domain of discourse is also expanded correspondingly.

According to a second aspect, an embodiment of the present disclosure provides a computer-readable storage medium. The computer-readable storage medium stores a computer program. When the computer program is executed, the AGP intelligent interpretation and insulin adjustment method based on an expert system in the first aspect is implemented.

According to a third aspect, an embodiment of the present disclosure provides a storage device, including a storage medium and a processor. The storage medium stores a computer program. When the computer program is executed, the AGP intelligent interpretation and insulin adjustment method based on an expert system in the first aspect is implemented.

Those skilled in the art should understand that the embodiments of the present disclosure may be provided as a method, a system, or a computer program product. Therefore, the present disclosure may use a form of hardware only embodiments, software only embodiments, or embodiments with a combination of software and hardware. Moreover, the present disclosure may use a form of a computer program product that is implemented on at least one computer-usable storage medium (including but not limited to a magnetic disk memory, a CD-ROM, an optical memory, and the like) that include computer-usable program code.

Obviously, those skilled in the art can make various alterations and modifications to the present disclosure without departing from the spirit and scope of the present disclosure. The present disclosure is intended to cover these modifications and variations provided that they fall within the scope of protection defined by the following claims and their equivalent technologies.

Although the embodiments of the present disclosure are illustrated above, it should be understood that the above embodiments are merely illustrative and may not be construed as limiting the scope of the present disclosure. Changes, modifications, substitutions and variations may be made to the above embodiments by a person of ordinary skill in the art within the scope of the present disclosure.

What is claimed is:

1. An ambulatory glucose profile (AGP) intelligent interpretation and insulin adjustment method based on an expert system for diabetic patients, comprising:

based on an AGP and an inference mechanism of a top-down forward inference strategy, establishing a knowledge base in the inference mechanism;

constructing an interpretation and decision support expert system with a simplified expert system architecture based on the knowledge base;

based on a fault tree analysis (FTA) method and an expert guideline, constructing a patient problem analysis tree in three dimensions of hypoglycemia, blood glucose fluctuation, and hyperglycemia of patients, wherein each branch of the patient problem analysis tree is corresponding to one or more rules;

expanding each rule with expert AGP interpretation and empirical data;

grouping the patients with a K-means clustering algorithm by extracting, for a continuous glucose monitor (CGM) matrix of the patients, glucose symbolic pattern (GSP) features based on domain knowledge and dividing the patients into four subtype groups T1, T2, T3, and T4 according to clinical significance;

constructing a basal insulin dosage adjustment rule and a mealtime insulin dosage adjustment rule based on an interval type-2 fuzzy expert system by taking, as system input indexes of the basal insulin dosage adjustment rule, a fasting blood-glucose (FBG) median, a proportion of days with nocturnal blood glucose in a hypoglycemic range, a proportion of days with nocturnal blood glucose elevated, and a proportion of days with nocturnal blood glucose in a hyperglycemic range, by taking, as system input indexes of the mealtime insulin dosage adjustment rule, a median for differences between 2–h postprandial blood glucose and preprandial blood glucose over a plurality of days, a proportion of days with next preprandial blood glucose or pre-sleep blood glucose in a hypoglycemic range, and a proportion of days with the next preprandial blood glucose or the pre-sleep blood glucose in an FBG elevated range, and by assuming a basal insulin adjusted dosage and a mealtime insulin adjusted dosage as system outputs, wherein constructing the basal insulin dosage adjustment rule and the mealtime insulin dosage adjustment rule comprises establishing a membership function for each of the system input indexes with an interval type-2 fuzzy set dominated by a triangle and followed by a trapezoid, formulating the basal insulin dosage adjustment rule with a fuzzy logic based on the membership functions preferentially according to probabilities of hyperglycemia and hypoglycemia at nighttime and then according to the FBG median, and formulating the mealtime insulin dosage adjustment rule with the fuzzy logic based on the membership functions preferentially according to probabilities of hyperglycemia and hypoglycemia before a next meal or a next sleep and then according to the median for the differences between the 2-h postprandial blood glucose and the preprandial blood glucose; and adjusting a node of the patient problem analysis tree based on the interpretation and decision support expert system and a group of the patients, wherein adjusting the node comprises selecting, according to the group of the patients, an insulin dosage adjustment node K1 for the subtype groups T2 and T3 and a conservative insulin adjustment node K2 for the subtype groups T1 and T4, the insulin dosage adjustment node K1 outputting an accurate dosage according to fuzzy inference and the conservative insulin adjustment node K2 decreasing or increasing dosage according to a blood glucose level, and determining, by fuzzy inference using the established membership functions, the corresponding system input indexes, and, the basal insulin dosage adjustment rule and the mealtime insulin dosage adjustment rule, the basal insulin adjusted dosage or the mealtime insulin adjusted dosage, and adjusting basal insulin or mealtime insulin of the patients according to the determined basal insulin adjusted dosage or mealtime insulin adjusted dosage, wherein adjusting basal insulin or mealtime insulin comprises reducing or increasing basal insulin of the patients or decreasing or increasing insulin at breakfast, lunch, or dinner of the patients, wherein the simplified expert system architecture comprises the knowledge base, a database, a human-machine interface (HMI), and the inference mechanism;

the knowledge base is configured to store a patient interpretation rule and a decision rule based on the AGP;

the database is configured to store personal information and blood glucose data of the patients;

the HMI is configured to transmit information of the patients to the interpretation and decision support expert system and display an AGP report; and the inference mechanism is configured to perform inference with the basal insulin dosage adjustment rule and the mealtime insulin dosage adjustment rule and an index calculated from data in the knowledge base to obtain a content of the AGP report of the patients and output the content.

2. The AGP intelligent interpretation and insulin adjustment method based on the expert system according to claim 1, wherein the establishing the knowledge base in the inference mechanism comprises:

checking data sufficiency, viewing an overall blood glucose level, and evaluating a hypoglycemia risk, glycemic variability (GV), and a hyperglycemia risk, thereby obtaining the knowledge base in the inference mechanism.

3. The AGP intelligent interpretation and insulin adjustment method based on the expert system according to claim 1, wherein the grouping the patients with the K-means clustering algorithm comprises:

for a continuous glucose monitor (CGM) matrix $X \in R^{M \times N}$ of the patients, extracting glucose symbolic pattern (GSP) features based on domain knowledge;

with the GSP features as an input, obtaining possible clusters of the patients by using a K-means clustering algorithm, taking K=4 as a final class number, and inputting the GSP features and a K value to the K-means clustering algorithm; and until the K-means clustering algorithm converges, outputting clusters of the patients, and dividing the patients into four subtype groups T1, T2, T3, and T4 according to clinical significance.

4. The AGP intelligent interpretation and insulin adjustment method based on the expert system according to claim 1, wherein the constructing the basal insulin dosage adjustment rule based on the interval type-2 fuzzy expert system comprises:

in combination with a basal insulin adjustment rule, taking a fasting blood-glucose (FBG) median, a proportion of days with nocturnal blood glucose in a hypoglycemic range, a proportion of days with the nocturnal blood glucose elevated, and a proportion of days with the nocturnal blood glucose in a hyperglycemic range as system input indexes;

taking 7.2 mmol/L as a cutoff point for elevated FBG of patients with type 1 diabetes or type 2 diabetes, calculating daily FBG according to mean blood glucose (MBG) in a range [6, min($t_z$, 8)], and assuming a basal insulin adjusted dosage as a system output, wherein $t_z$ is a breakfast starting time predicted through a mealtime detection algorithm, and the mealtime detection algorithm is implemented by generating and preprocessing a dataset, training a neural network to obtain an optimal model, and applying the optimal model to a test set to filter and output a most possible mealtime point to serve as the breakfast starting time;

establishing a membership function for each of the system input indexes with an interval type-2 fuzzy set dominated by a triangle and followed by a trapezoid; and formulating a rule for dosage adjustment on basal insulin of the patients with a fuzzy logic based on the membership function, wherein the rule is preferentially formulated according to probabilities of the hyperglycemia and the hypoglycemia at nighttime, and then the rule is formulated for the dosage adjustment according to the FBG median.

5. The AGP intelligent interpretation and insulin adjustment method based on the expert system according to claim 1, wherein the constructing the mealtime insulin dosage adjustment rule based on the interval type-2 fuzzy expert system comprises:

in combination with a mealtime insulin adjustment rule, taking a median for differences between 2-h postprandial blood glucose and preprandial blood glucose over a plurality of days, a proportion of days with next preprandial blood glucose or pre-sleep blood glucose in a hypoglycemic range, and a proportion of days with the next preprandial blood glucose or the pre-sleep blood glucose in an FBG elevated range as system input indexes;

calculating the difference between the 2-h postprandial blood glucose and the preprandial blood glucose according to a difference between a blood glucose value 2 h after mealtime and a blood glucose value 30 min before the mealtime, and assuming a mealtime insulin adjusted dosage as a system output;

establishing a membership function for each of the system input indexes with an interval type-2 fuzzy set dominated by a triangle and followed by a trapezoid; and formulating a rule for dosage adjustment on mealtime insulin of a diabetic patient with a fuzzy logic based on the membership function, wherein the rule is preferentially formulated according to probabilities of the hyperglycemia and the hypoglycemia before a next meal or a next sleep, and then the rule is formulated for the dosage adjustment according to the median for the differences between the 2-h postprandial blood glucose and the preprandial blood glucose.

6. The AGP intelligent interpretation and insulin adjustment method based on the expert system according to claim 1, further comprising:

when an insulin dosage adjustment suggestion is adopted by the patients in a previous period to adjust basal insulin α IU and mealtime insulin β IU, calculating suggested basal insulin λ IU and suggested mealtime insulin γ IU with the interval type-2 fuzzy expert system of the previous period in a present period; and updating parameters of a membership function based on λ and γ, and determining an insulin dosage adjustment suggestion in the present period based on an updated membership function.

7. A non-transitory computer-readable storage medium, including at least one of a magnetic disk memory, a CD-ROM, or an optical memory, storing a computer program, wherein when the computer program is executed by a processor, the AGP intelligent interpretation and insulin adjustment method based on the expert system according to claim 1 is implemented.

8. The non-transitory computer-readable storage medium according to claim 7, wherein in the AGP intelligent interpretation and insulin adjustment method based on the expert system, the establishing the knowledge base in the inference mechanism comprises:

checking data sufficiency, viewing an overall blood glucose level, and evaluating a hypoglycemia risk, GV, and a hyperglycemia risk, thereby obtaining the knowledge base in the inference mechanism.

9. The non-transitory computer-readable storage medium according to claim 7, wherein in the AGP intelligent interpretation and insulin adjustment method based on the expert system, the grouping the patients with the K-means clustering algorithm comprises:

for a CGM matrix $X \in R^{M \times N}$ of the patients, extracting GSP features based on domain knowledge;

with the GSP features as an input, obtaining possible clusters of the patients by using a K-means clustering algorithm, taking K=4 as a final class number, and inputting the GSP features and a K value to the K-means clustering algorithm; and until the K-means clustering algorithm converges, outputting clusters of the patients, and dividing the patients into four subtype groups T1, T2, T3, and T4 according to clinical significance.

10. The non-transitory computer-readable storage medium according to claim 7, wherein in the AGP intelligent interpretation and insulin adjustment method based on the expert system, the constructing the basal insulin dosage adjustment rule based on the interval type-2 fuzzy expert system comprises:

in combination with a basal insulin adjustment rule, taking an FBG median, a proportion of days with nocturnal blood glucose in a hypoglycemic range, a proportion of days with the nocturnal blood glucose elevated, and a proportion of days with the nocturnal blood glucose in a hyperglycemic range as system input indexes;

taking 7.2 mmol/L as a cutoff point for elevated FBG of patients with type 1 diabetes or type 2 diabetes, calculating daily FBG according to MBG in a range [6, min $(t_z, 8)$], and assuming a basal insulin adjusted dosage as a system output, wherein $t_z$ is a breakfast starting time predicted through a mealtime detection algorithm, and the mealtime detection algorithm is implemented by generating and preprocessing a dataset, training a neural network to obtain an optimal model, and applying the optimal model to a test set to filter and output a most possible mealtime point to serve as the breakfast starting time;

establishing a membership function for each of the system input indexes with an interval type-2 fuzzy set dominated by a triangle and followed by a trapezoid; and formulating a rule for dosage adjustment on basal insulin of the patients with a fuzzy logic based on the membership function, wherein the rule is preferentially formulated according to probabilities of the hyperglycemia and the hypoglycemia at nighttime, and then the rule is formulated for the dosage adjustment according to the FBG median.

11. The non-transitory computer-readable storage medium according to claim 7, wherein in the AGP intelligent interpretation and insulin adjustment method based on the expert system, the constructing the mealtime insulin dosage adjustment rule based on the interval type-2 fuzzy expert system comprises:

in combination with a mealtime insulin adjustment rule, taking a median for differences between 2-h postprandial blood glucose and preprandial blood glucose over a plurality of days, a proportion of days with next preprandial blood glucose or pre-sleep blood glucose in a hypoglycemic range, and a proportion of days with the next preprandial blood glucose or the pre-sleep blood glucose in an FBG elevated range as system input indexes;

calculating the difference between the 2-h postprandial blood glucose and the preprandial blood glucose according to a difference between a blood glucose value 2 h after mealtime and a blood glucose value 30 min before the mealtime, and assuming a mealtime insulin adjusted dosage as a system output;

establishing a membership function for each of the system input indexes with an interval type-2 fuzzy set dominated by a triangle and followed by a trapezoid; and formulating a rule for dosage adjustment on mealtime insulin of a diabetic patient with a fuzzy logic based on the membership function, wherein the rule is preferentially formulated according to probabilities of the hyperglycemia and the hypoglycemia before a next meal or a next sleep, and then the rule is formulated for the dosage adjustment according to the median for the differences between the 2-h postprandial blood glucose and the preprandial blood glucose.

12. The non-transitory computer-readable storage medium according to claim 7, wherein in the AGP intelligent interpretation and insulin adjustment method based on the expert system, further comprising:

when an insulin dosage adjustment suggestion is adopted by the patients in a previous period to adjust basal insulin α IU and mealtime insulin β IU, calculating suggested basal insulin λ IU and suggested mealtime insulin γ IU with the interval type-2 fuzzy expert system of the previous period in a present period; and updating parameters of a membership function based on λ and γ, and determining an insulin dosage adjustment suggestion in the present period based on an updated membership function.

13. A storage device, comprising a storage medium and a processor, wherein the storage medium stores a computer program; and when the processor executes the computer program, the AGP intelligent interpretation and insulin adjustment method based on the expert system according to claim 1 is implemented.

14. The storage device according to claim 13, wherein in the AGP intelligent interpretation and insulin adjustment method based on the expert system, the establishing the knowledge base in the inference mechanism comprises:

checking data sufficiency, viewing an overall blood glucose level, and evaluating a hypoglycemia risk, GV, and a hyperglycemia risk, thereby obtaining the knowledge base in the inference mechanism.

15. The storage device according to claim 13, wherein in the AGP intelligent interpretation and insulin adjustment method based on the expert system, the grouping the patients with the K-means clustering algorithm comprises:

for a CGM matrix $X \in R^{M \times N}$ of the patients, extracting GSP features based on domain knowledge;

with the GSP features as an input, obtaining possible clusters of the patients by using a K-means clustering algorithm, taking K=4 as a final class number, and inputting the GSP features and a K value to the K-means clustering algorithm; and until the K-means clustering algorithm converges, outputting clusters of the patients, and dividing the patients into four subtype groups T1, T2, T3, and T4 according to clinical significance.

16. The storage device according to claim 13, wherein in the AGP intelligent interpretation and insulin adjustment method based on the expert system, the constructing the basal insulin dosage adjustment rule based on the interval type-2 fuzzy expert system comprises:

in combination with a basal insulin adjustment rule, taking an FBG median, a proportion of days with nocturnal blood glucose in a hypoglycemic range, a proportion of days with the nocturnal blood glucose elevated, and a proportion of days with the nocturnal blood glucose in a hyperglycemic range as system input indexes;

taking 7.2 mmol/L as a cutoff point for elevated FBG of patients with type 1 diabetes or type 2 diabetes, calculating daily FBG according to MBG in a range [6, min ($t_z$, 8)], and assuming a basal insulin adjusted dosage as a system output, wherein $t_z$ is a breakfast starting time predicted through a mealtime detection algorithm, and the mealtime detection algorithm is implemented by generating and preprocessing a dataset, training a neural network to obtain an optimal model, and applying the optimal model to a test set to filter and output a most possible mealtime point to serve as the breakfast starting time;

establishing a membership function for each of the system input indexes with an interval type-2 fuzzy set dominated by a triangle and followed by a trapezoid; and formulating a rule for dosage adjustment on basal insulin of the patients with a fuzzy logic based on the membership function, wherein the rule is preferentially formulated according to probabilities of the hyperglycemia and the hypoglycemia at nighttime, and then the rule is formulated for the dosage adjustment according to the FBG median.

17. The storage device according to claim 13, wherein in the AGP intelligent interpretation and insulin adjustment method based on the expert system, the constructing the mealtime insulin dosage adjustment rule based on the interval type-2 fuzzy expert system comprises:

in combination with a mealtime insulin adjustment rule, taking a median for differences between 2-h postprandial blood glucose and preprandial blood glucose over a plurality of days, a proportion of days with next preprandial blood glucose or pre-sleep blood glucose in a hypoglycemic range, and a proportion of days with the next preprandial blood glucose or the pre-sleep blood glucose in an FBG elevated range as system input indexes;

calculating the difference between the 2-h postprandial blood glucose and the preprandial blood glucose according to a difference between a blood glucose value 2 h after mealtime and a blood glucose value 30 min before the mealtime, and assuming a mealtime insulin adjusted dosage as a system output;

establishing a membership function for each of the system input indexes with an interval type-2 fuzzy set dominated by a triangle and followed by a trapezoid; and formulating a rule for dosage adjustment on mealtime insulin of a diabetic patient with a fuzzy logic based on the membership function, wherein the rule is preferentially formulated according to probabilities of the hyperglycemia and the hypoglycemia before a next meal or a next sleep, and then the rule is formulated for the dosage adjustment according to the median for the differences between the 2-h postprandial blood glucose and the preprandial blood glucose.

18. The storage device according to claim 13, wherein in the AGP intelligent interpretation and insulin adjustment method based on the expert system, further comprising:

when an insulin dosage adjustment suggestion is adopted by the patients in a previous period to adjust basal insulin $\alpha$ IU and mealtime insulin $\beta$ IU, calculating suggested basal insulin $\lambda$ IU and suggested mealtime insulin $\gamma$ IU with the interval type-2 fuzzy expert system of the previous period in a present period; and updating parameters of a membership function based on $\lambda$ and $\gamma$, and determining an insulin dosage adjustment suggestion in the present period based on an updated membership function.

* * * * *